United States Patent
Uno et al.

(10) Patent No.: US 9,453,766 B2
(45) Date of Patent: Sep. 27, 2016

(54) MANAGEMENT SYSTEM

(71) Applicant: FUJITSU LIMITED, Kawasaki-shi, Kanagawa (JP)

(72) Inventors: Kazushi Uno, Atsugi (JP); Fumio Takei, Isehara (JP); Takeo Kasajima, Machida (JP); Hiroyuki Fukuda, Yokohama (JP); Takahiro Arioka, Isehara (JP)

(73) Assignee: FUJITSU LIMITED, Kawasaki (JP)

( * ) Notice: Subject to any disclaimer, the term of this patent is extended or adjusted under 35 U.S.C. 154(b) by 0 days.

(21) Appl. No.: 14/964,990

(22) Filed: Dec. 10, 2015

(65) Prior Publication Data

US 2016/0178440 A1 Jun. 23, 2016

(30) Foreign Application Priority Data

Dec. 19, 2014 (JP) ................................. 2014-257376

(51) Int. Cl.
*G01J 5/48* (2006.01)
*G01J 5/00* (2006.01)
*G01J 5/32* (2006.01)
*G01J 5/02* (2006.01)

(52) U.S. Cl.
CPC .............. *G01J 5/0025* (2013.01); *G01J 5/027* (2013.01); *G01J 5/32* (2013.01); *G01J 2005/0077* (2013.01)

(58) Field of Classification Search
CPC .......... G01J 5/08; G01J 5/0003; G01J 5/041; G01J 5/60; G01J 5/0022
USPC ......................................................... 356/43
See application file for complete search history.

(56) References Cited

U.S. PATENT DOCUMENTS

| 6,870,643 | B2* | 3/2005 | Thompson | H04N 1/405 345/596 |
|---|---|---|---|---|
| 7,606,437 | B2* | 10/2009 | Gallagher | G06F 17/30265 382/254 |
| 7,881,628 | B2* | 2/2011 | Itagaki | G03G 15/0173 399/49 |
| 2003/0109058 | A1* | 6/2003 | Bolam | A61K 49/1815 436/173 |
| 2010/0185087 | A1* | 7/2010 | Nields | A61B 18/18 600/439 |
| 2010/0244833 | A1 | 9/2010 | Sakakura | |
| 2012/0053445 | A1* | 3/2012 | Turnquist | A61B 5/01 600/407 |

FOREIGN PATENT DOCUMENTS

| JP | 2009-210501 | 9/2009 |
|---|---|---|
| JP | 2010-253266 | 11/2010 |

* cited by examiner

*Primary Examiner* — Tarifur Chowdhury
*Assistant Examiner* — Md M Rahman
(74) *Attorney, Agent, or Firm* — Fujitsu Patent Center

(57) ABSTRACT

A management system includes labels disposed on a management target at respective positions different from each other each of the labels including display parts, the display parts changing respective colors depending on different levels of temperature or humidity, the display parts changing coloring positions depending on the level; an image obtaining unit outputting image data indicating an image of the labels captured by the imaging device; an image processing part performing first or second image processing, the first image processing transforming the image data so that a difference in a number of pixels corresponding to each of the labels among the labels in image data after the transformation is less than that before the transformation, the second image processing recognizing an image of the display parts; and a level detector detecting the level of temperature or humidity based on brightness information of pixels corresponding to the display parts.

15 Claims, 27 Drawing Sheets

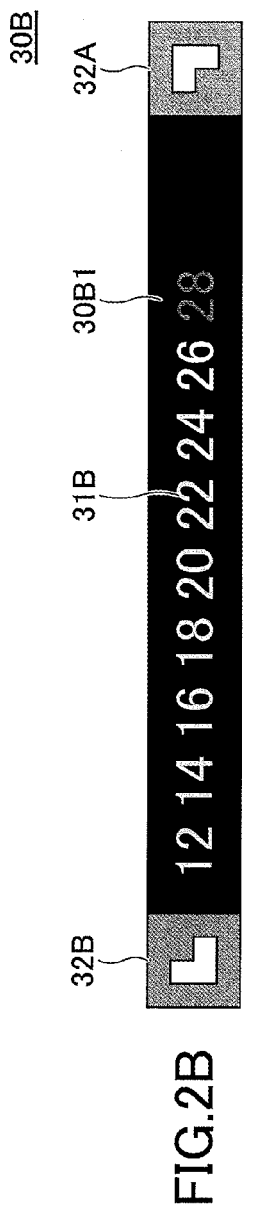
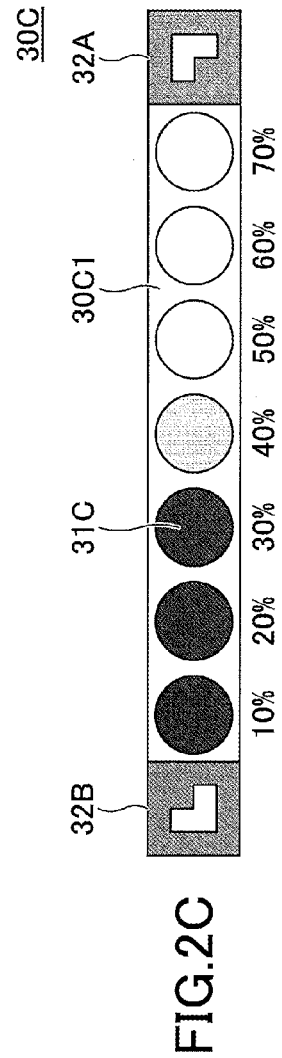
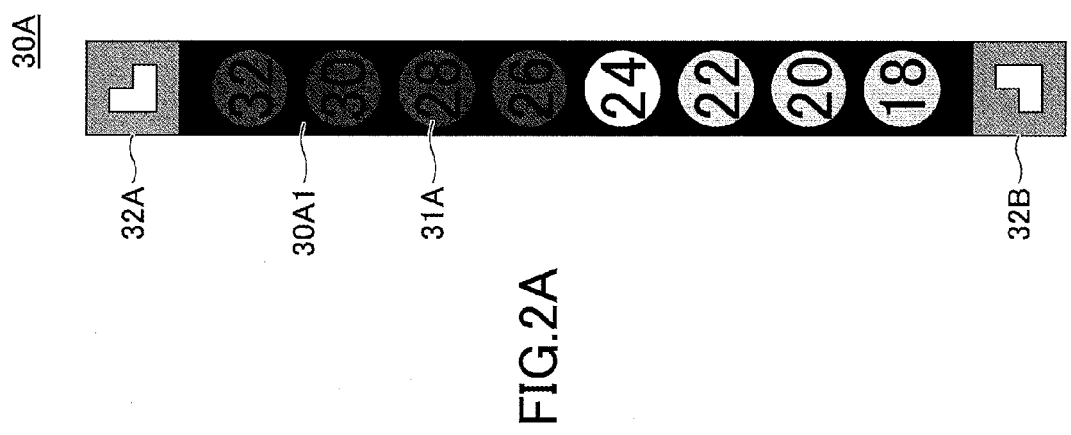

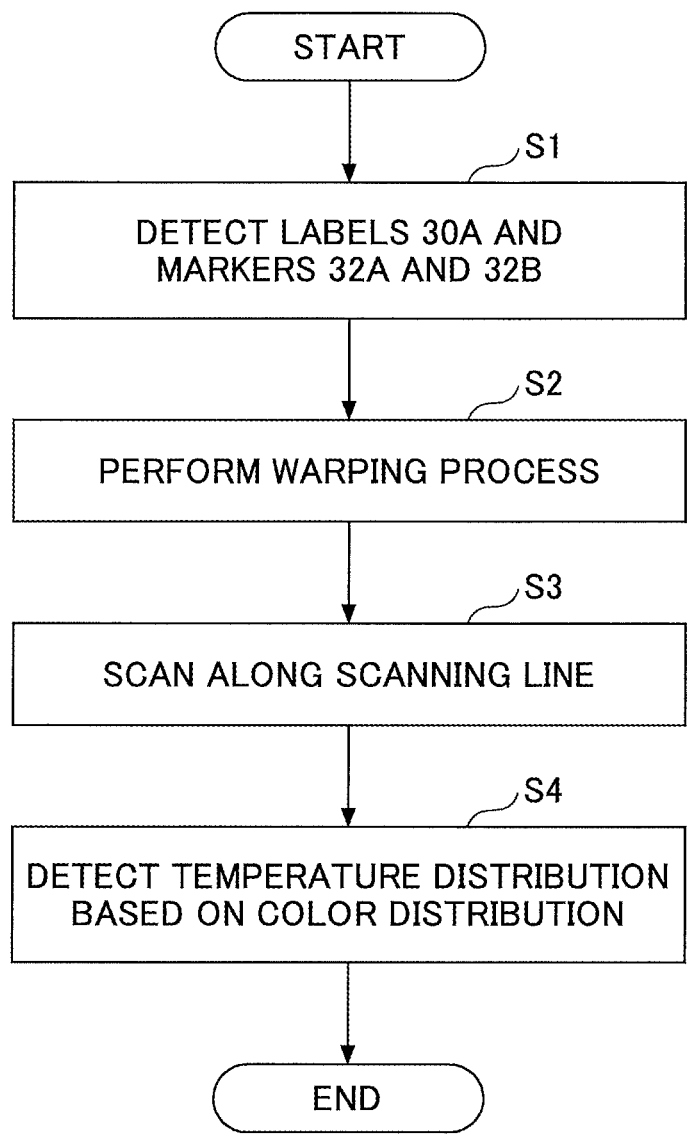

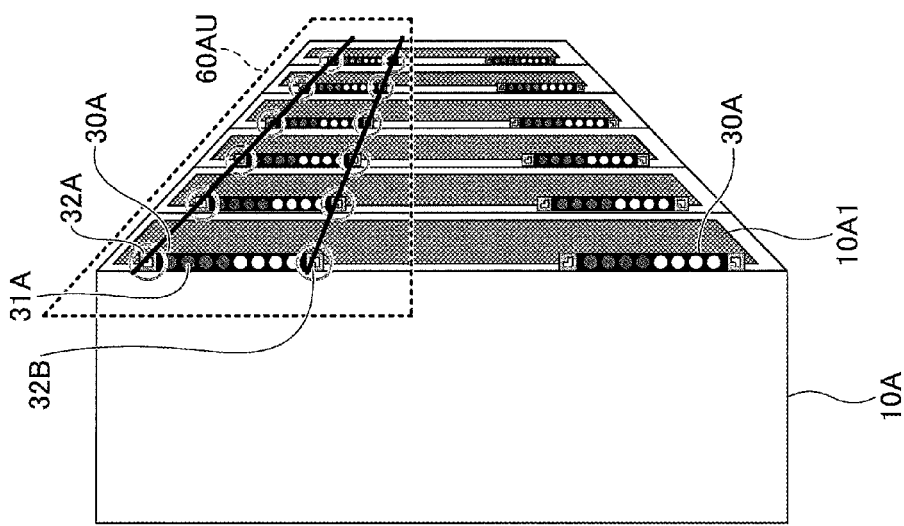
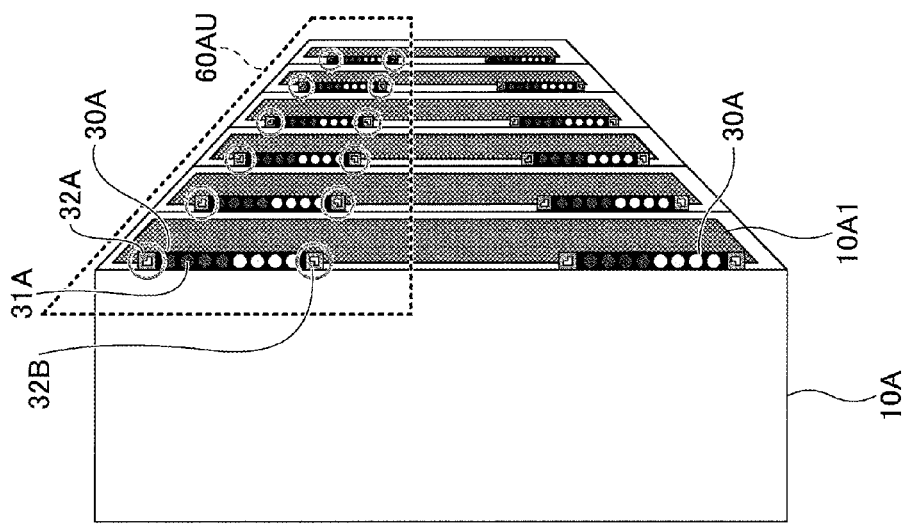
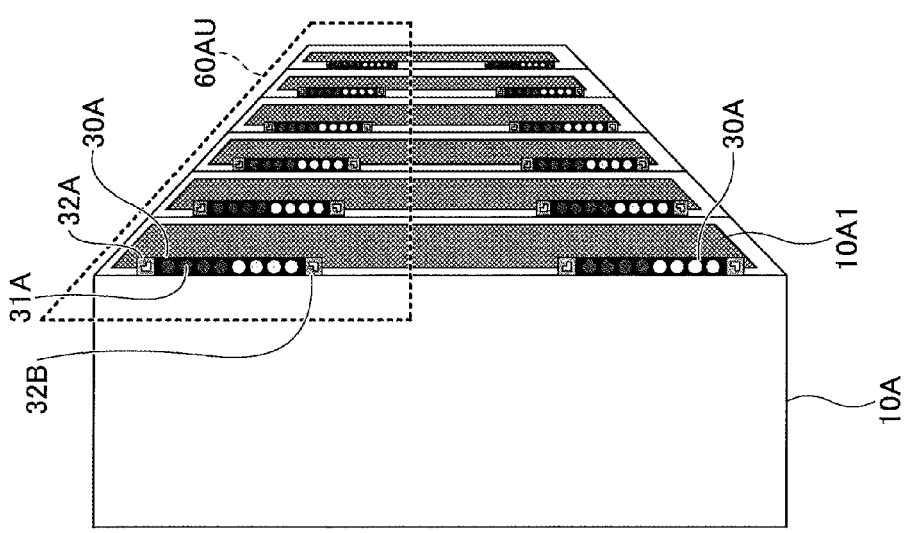

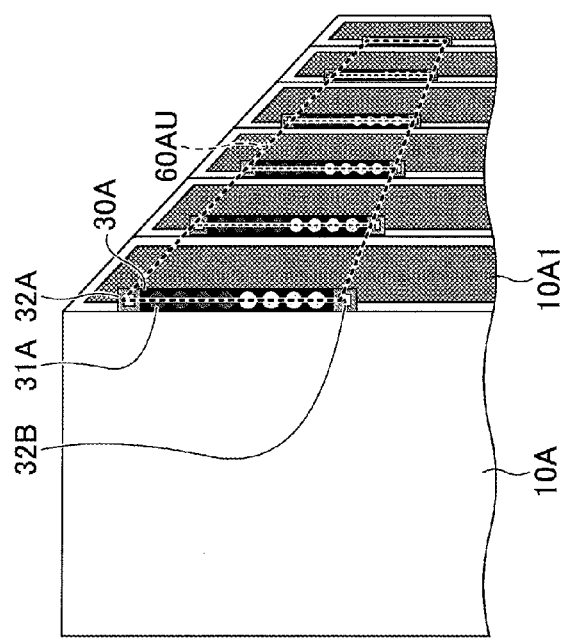
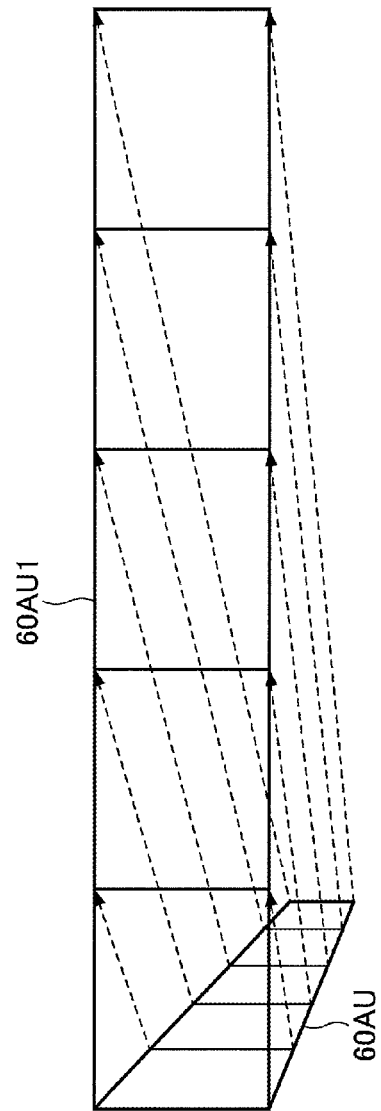
FIG.13A
FIG.13B

FIG.20B

| LABEL NO. | FOCAL LENGTH (ZOOM SETTING) f1 | FOCAL LENGTH (ZOOM SETTING) f2 |
|---|---|---|
| 1 | WIDTH H_1_1 (pixels)<br>LENGTH V_1_1 (pixels)<br>FILE NAME: model_1_1 | WIDTH H_2_1 (pixels)<br>LENGTH V_2_1 (pixels)<br>FILE NAME: model_2_1 |
| 2 | WIDTH H_1_2 (pixels)<br>LENGTH V_1_2 (pixels)<br>FILE NAME: model_1_2 | WIDTH H_2_2 (pixels)<br>LENGTH V_2_2 (pixels)<br>FILE NAME: model_2_2 |
| 3 | WIDTH H_1_3 (pixels)<br>LENGTH V_1_3 (pixels)<br>FILE NAME: model_1_3 | WIDTH H_2_3 (pixels)<br>LENGTH V_2_3 (pixels)<br>FILE NAME: model_2_3 |
| 4 | WIDTH H_1_4 (pixels)<br>LENGTH V_1_4 (pixels)<br>FILE NAME: model_1_4 | WIDTH H_2_4 (pixels)<br>LENGTH V_2_4 (pixels)<br>FILE NAME: model_2_4 |
| 5 | WIDTH H_1_5 (pixels)<br>LENGTH V_1_5 (pixels)<br>FILE NAME: model_1_5 | WIDTH H_2_5 (pixels)<br>LENGTH V_2_5 (pixels)<br>FILE NAME: model_2_5 |
| 6 | WIDTH H_1_6 (pixels)<br>LENGTH V_1_6 (pixels)<br>FILE NAME: model_1_6 | WIDTH H_2_6 (pixels)<br>LENGTH V_2_6 (pixels)<br>FILE NAME: model_2_6 |

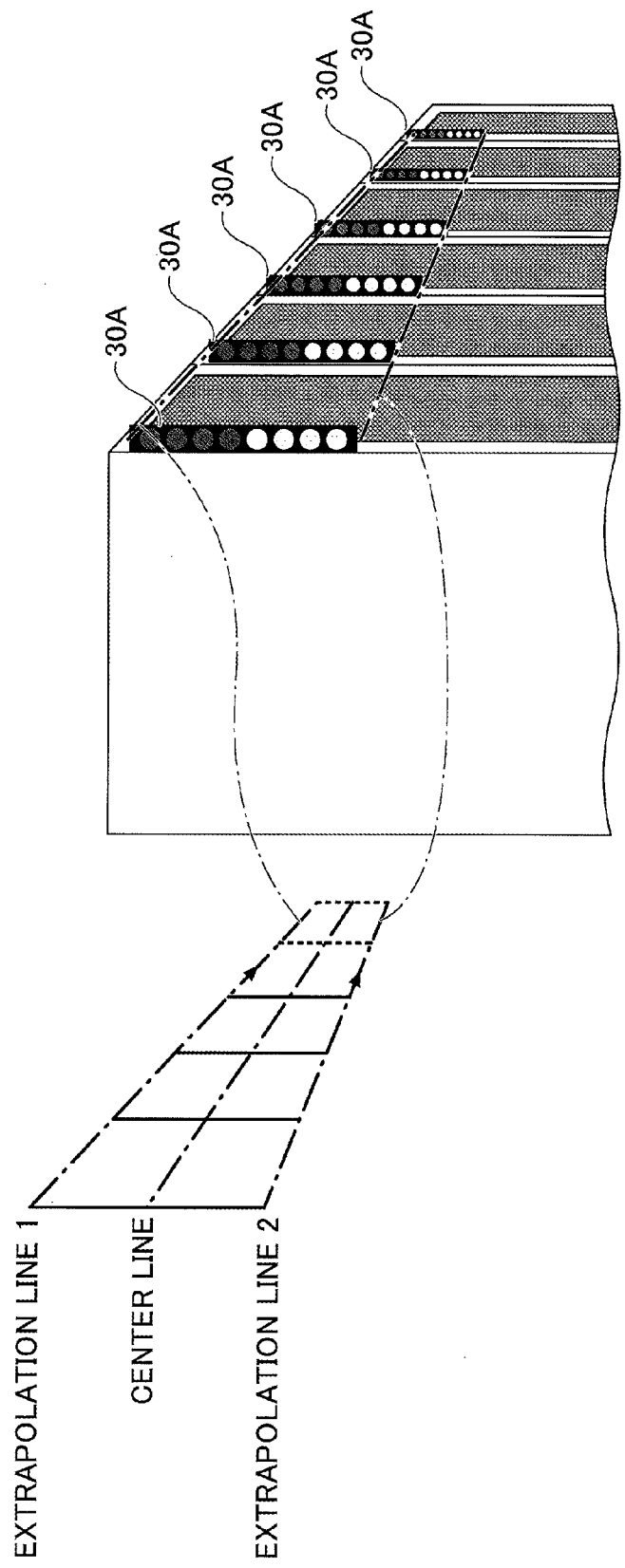

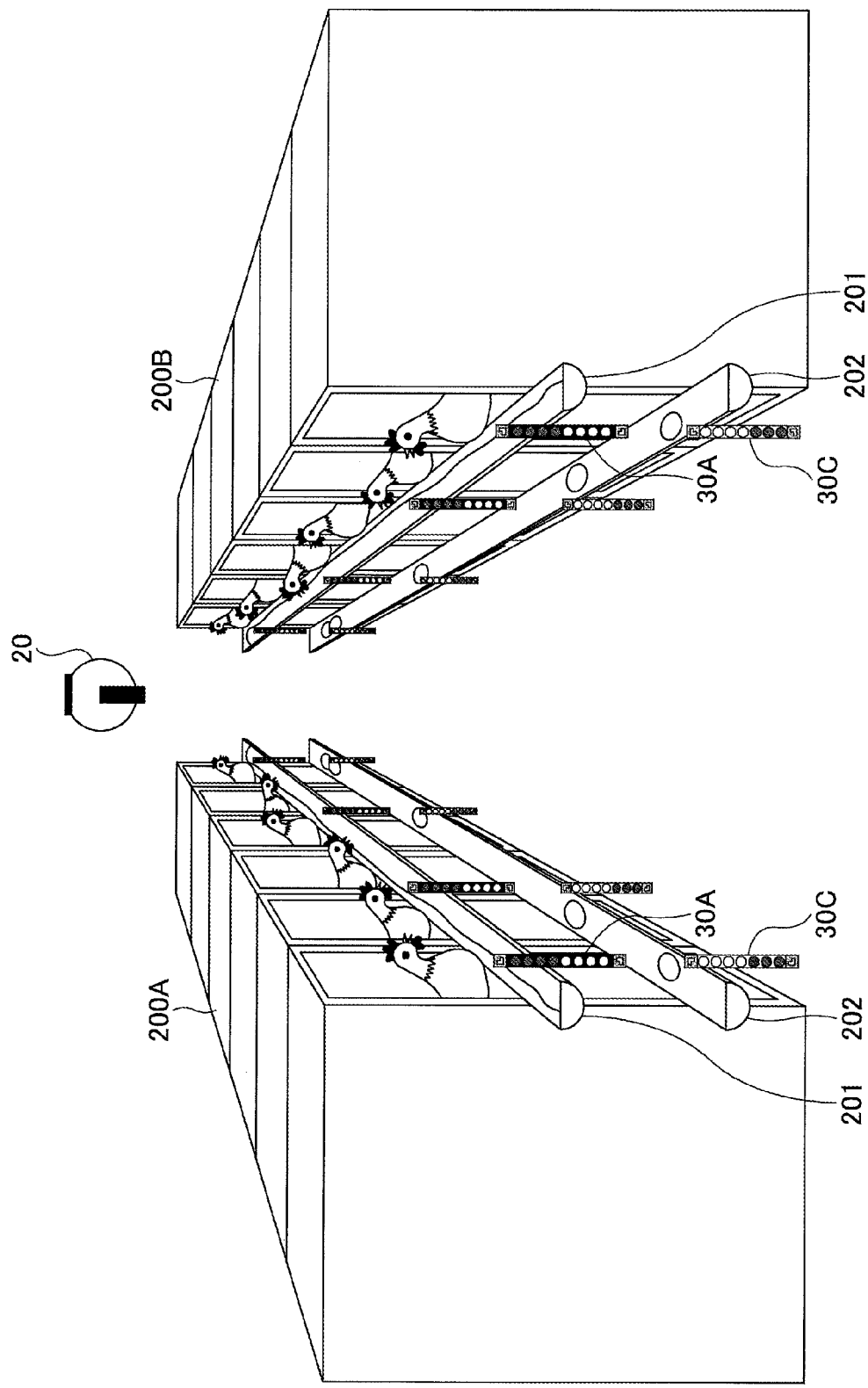

MANAGEMENT SYSTEM

CROSS-REFERENCE TO RELATED APPLICATION

This application is based upon and claims the benefit of priority of the prior Japanese Patent Application No. 2014-257376, filed on Dec. 19, 2014, the entire contents of which are incorporated herein by reference.

FIELD

The embodiment discussed herein is related to a management system.

BACKGROUND

Conventionally, there has been known an Magnetic Resonance Imaging (MRI) machine which includes a static magnetic field generator, which applies a static magnetic field to a patient under test who is inserted in a patient resident space (patient bore), a gradient magnetic field generator, which applies a gradient magnetic field to the patient under test, and a high-frequency pulse transmitter which applies a high-frequency magnetic field so that nuclear magnetic resonance (NMR) is excited in the nucleus of the atoms in the tissues of the patient under test. The MRI machine further includes an image data generator, which generates a tomographic image relative to the patient under test in the patient resident space by using a signal produced by the nuclear magnetic resonance (NMR), a detector, which detects the temperature distribution in the patient resident space from the outside of the patient resident space, and a determinator which determines whether there exists a part where the temperature, which is based on the temperature distribution, is higher than or equal to a threshold value which is set in advance. The MRI machine further includes a controller which controls the gradient magnetic field generator to stop applying the gradient magnetic field to the patient under test when the determinator determines that there exists a part where the temperature, which is based on the temperature distribution, is higher than or equal to the threshold value (see, for example, Japanese Laid-open Patent Publication No. 2010-253266).

The detector captures a temperature distribution image, which indicates the temperature distribution, or obtains an image of thermal labels (thermo-labels) or thermal paints by using a thermography camera.

Recently, it has become more and more popular that many computers (e.g., servers) are installed in the same room and collectively managed in, for example, a data center which manages and operates client's information or a computer center which handles many jobs (JOB) of the own company (hereinafter collectively called a "data center").

In the data center, many racks are set (installed) in a room, and a plurality of computers are mounted in each of the racks. Under such circumstance, massive heat is generated from the computers and the temperature in the racks is increased, which may cause a malfunction or failure. Therefore, air-conditioning equipment is used to manage the temperature in the room by introducing cool air of the room into the racks by using fans, etc., to lower the temperature of the computers so that the temperature in the room is not increased due to the heat transferred from the rack.

SUMMARY

According to an aspect of the present invention, a management system includes a plurality of labels disposed on a management target at respective positions different from each other in a direction separating from an imaging device, each of the labels including a plurality of display parts, the plurality of display parts changing respective colors depending on different levels of temperature or humidity with each other, the plurality of display parts being arranged so as to change coloring positions depending on level of temperature or humidity; an image obtaining unit outputting image data indicating an image of the labels captured by the imaging device; an image processing part performing first image processing or second image processing, the first image processing transforming the image data in a manner such that a difference in a number of pixels corresponding to each of the labels among the labels in image data after the transformation is less than a difference in the number of pixels corresponding to each of the labels among the labels in the image data before the transformation, the second image processing recognizing an image of the plurality of display parts by using information of the number of pixels corresponding to each of the labels in the image data; and a level detector detecting the level of temperature or humidity based on brightness information of pixels corresponding to the display parts, the brightness information obtained by performing the first image processing or the second image processing by the image processing part on the image data output from the image obtaining unit.

The objects and advantages of the embodiments disclosed herein will be realized and attained by means of the elements and combinations particularly pointed out in the claims.

It is to be understood that both the foregoing general description and the following detailed description are exemplary and explanatory and are not restrictive of the invention as claimed.

BRIEF DESCRIPTION OF DRAWINGS

FIG. 2A illustrates a label 30A which is used in the management system according to the first embodiment;

FIG. 2B illustrates a label 30B which is used in the management system according to the first embodiment;

FIG. 2C illustrates a label 30C which is used in the management system according to the first embodiment;

FIG. 8 is an example flowchart of a process executed by the control apparatus 50 included in the management system 100 according to the first embodiment;

FIG. 10A illustrates an example process performed on a region 60AU;

FIG. 10B illustrates an example process performed on the region 60AU;

FIG. 10C illustrates an example process performed on the region 60AU;

FIG. 13A illustrates a principle of the warping process by performing a perspective projection transformation;

FIG. 13B illustrates the principle of the warping process by performing the perspective projection transformation;

FIG. 20B illustrates the example method of deriving the interval between the labels 30A;

FIG. 20C illustrates the example method of deriving the interval between the labels 30A;

FIG. 22 illustrates an example inside of a poultry house;

DESCRIPTION OF EMBODIMENT

Figure 1A:
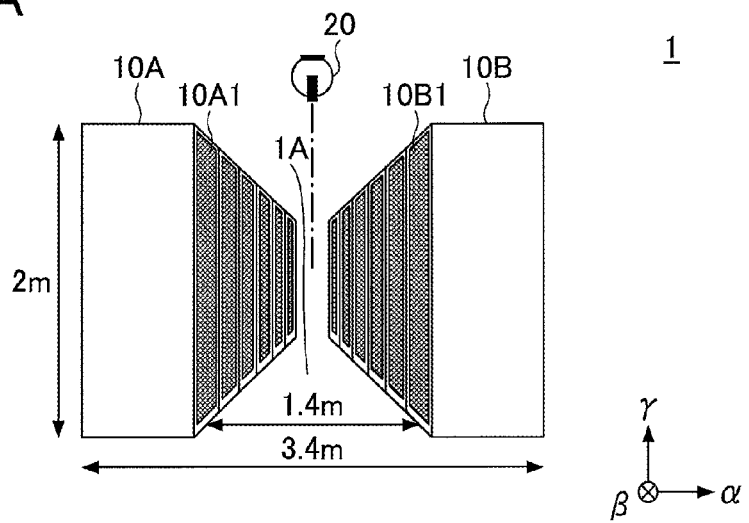
FIG. 1A illustrates a state of an inside of a data center 1 to which a management system according to a first embodiment is applied.

In related art technologies, in order to reduce the energy consumption in the data center while preventing a malfunction and failure of the computers in the data center due to heat, it is desired to continuously measure the temperature distribution in the data center and control the air-conditioning equipment to set an appropriate temperature in accordance with the measurement results. To measure the temperature distribution in the data center, for example, it is thought that many temperature sensor ICs or temperature sensors such as thermocouples are set (installed) both inside and outside the rack. In this case, however, the number of the temperature sensors becomes enormous, so that the cost of installing the temperature sensors becomes (very) high. Specifically, it is inevitable to increase, for example, (1) the cost of laying the sensor wires (in case of wired sensors), or (2) the cost of setting the transceivers for sensors (in case of wireless sensors), and (3) cost of associating the sensors with the setting positions.

When the number of the temperature sensors is increased, the rate of failure is high, and the temperature sensor where the failure is detected has to be replaced. Further, when the rack is removed, added, or moved, the corresponding construction cost and the operation cost become necessary. When such circumstances are considered, a system is desired where the construction costs of introducing and modifying the system and the associated operating cost can be minimized (reduced) and the maintenance cost can be minimized (reduced) by, for example, preventing (reducing) the occurrence of sensor failure.

The importance of finely measuring and managing the temperatures has been increased not only in the technical field of the data center but also in other various technical fields. For example, in the technical field of vinyl greenhouse cultivation of melons and strawberries, it is desired to effectively ensure the quality by performing multistep temperature management which is taken as measures to mitigate the increase of the fuel cost. Similarly, in the technical field of cold storage warehouses, it is desired to take measures to determine the stored goods to be managed for each of the temperature sections to reduce the freezing cost. Further, in the technical field of the semi-windowless poultry house where chickens are forced to lay eggs for a certain period, it is desired to take measures to effectively cause chickens to lay eggs by maintaining (providing) comfortable air conditioning for the chickens. In those example technical fields, it is desired to recognize the fine temperature distributions of the spaces in all sections. Furthermore, in those applications (technical fields), it is also desired to have fine humidity control in addition to the fine temperature control. In the technical fields, however, similar to the case of the data center, there exist the common (same) problems such as the costs of sensor wiring, installing the transceivers, associating with the system, managing failures, etc., when the sensors are installed. However, it is difficult to take measures to respond to the problems because of the (high) costs.

Furthermore, in another aspect, it is also desired to ensure security. The data center is getting involved in severe competition, so that the guarantee of the security is becoming an essential condition for each company (service provider) to acquire the business. Further, the theft risk of high-value-added agricultural products such as melons and strawberries is getting higher and higher, so that the number of farmers is increasing who consider the introduction of the system which transmits (sends an alarm of) the existence of an intruder to a mobile terminal. The desired security differs depending on the technical fields (applications). In the cold storage warehouse, it is desired to ensure the security of the people in the warehouse. On the other hand, in the semi-windowless poultry house, although the chickens are not stolen, it is desired to manage the symptom of bird influenza. However, only large-scale businesses can afford to introduce a monitoring camera system for that purpose only, and it is difficult for smaller businesses to introduce it due to the (high) cost.

When a monitoring camera is introduced for the monitoring purpose only, it may be expensive (in view of cost-effectiveness). Further, when a multi-point monitoring system is constructed, the introduction and maintenance costs are high which include the costs of (sensor) wiring, installing the transceivers, failure management, system association whenever the layout is changed, etc. To overcome the problem, as illustrated (described) in Japanese Laid-open Patent Publication No. 2010-253266, a method is proposed (known) in which an image of the thermal labels (thermolabels) or thermal paints is obtained. When the monitoring camera is used as a method of acquiring the image, the monitoring camera can also serve as the transceiver for sensing.

In a conventional MRI machine, it is possible to determine whether there exists a part where the temperature is increased to a predetermined threshold value set in advance or higher. Here, the predetermined threshold value is 41° C. or less. For example, by using a thermal label whose discoloring temperature is 40° C. or lower, when a part is generated where the temperature is 40° C. or higher, the operation of the MRI machine is stopped. This function is provided for ensuring the safety of the machine and the patient.

However, as described above, in a conventional MRI machine, it is possible to determine in each measurement point whether the temperature is increased to a certain temperature or higher. However, in a case where there is the possibility that the temperature differs in each measurement point, it is not possible to discretely measure the temperatures in each measurement point. Further, in a conventional MRI machine, it is not possible to measure humidity. Due to this, the technique used in the MRI machine cannot be used in the temperature and humidity monitoring applications such as, for example, the data center, and greenhouse horticulture applications.

According to an embodiment of the present invention, it is possible to provide a management system that can discretely measure the temperature or humidity in a plurality of measurement locations (points).

In the following, management systems according to embodiments of the present invention are described.

First Embodiment

Recently, it has become more and more popular that many computers (e.g., servers) are installed in the same room and collectively managed in, for example, a data center which manages and operates client's information or a computer center which handles many jobs (JOB) of the own company (hereinafter collectively called a "data center").

In the data center, many racks are set (installed) in a room, and a plurality of computers are mounted in each of the racks. Under such circumstance, massive heat is generated by the computers and the temperature in the racks is increased, which may cause a malfunction or failure. Therefore, air-conditioning equipment is used to manage the temperature in the room by introducing cool air of the room into the racks by using fans, etc., to lower the temperature of the computers in a way so that the temperature in the room is not increased due to the heat transferred from the rack.

FIG. 1 illustrates an example state of the inside of a data center (room) 1 to which a management system according to the first embodiment is applied.

In the data center 1, server racks 10A and 10B and a monitoring camera 20 are installed along a pathway 1A.

Figure 1B:
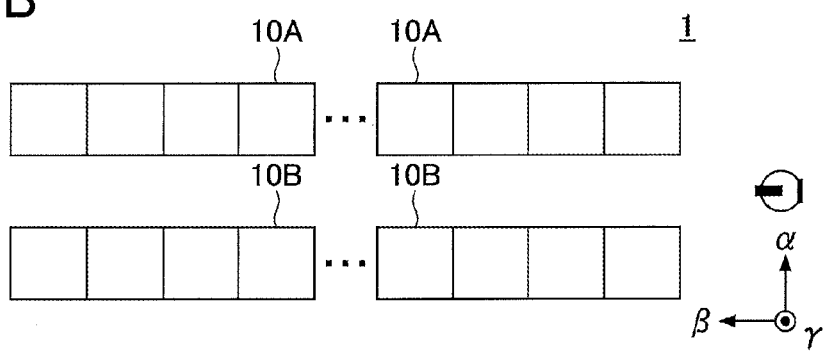
FIG. 1B illustrates a state of the inside of the data center 1 to which the management system according to a first embodiment is applied.
Figure 1C:
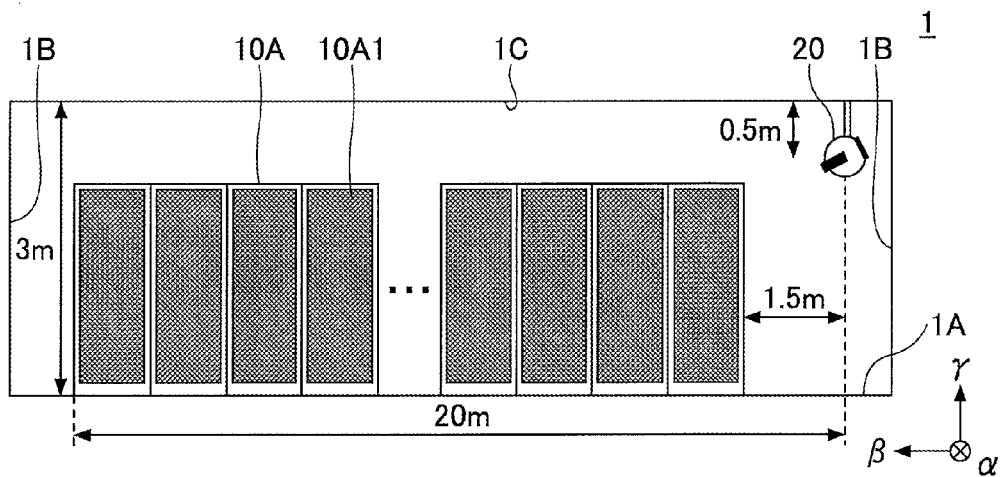
FIG. 1C illustrates a state of the inside of the data center 1 to which the management system according to a first embodiment is applied.

FIG. 1A illustrates the layout of the server racks 10A and 10B and the monitoring camera 20 installed along the pathway 1A. FIG. 1B illustrates the planer layout of FIG. 1A. FIG. 1C is a drawing of the server rack 10A viewed from the pathway 1A side. FIG. 1C further illustrates the pathway 1A on which the server racks 10A and 10B are disposed, inner walls 1B, and a ceiling 1C. The pathway 1A is a part of the floor of the room 1.

Further, here, as the orthogonal coordinate system, an αβγ coordinate system is defined. The α axis extends in the direction where the server racks 10A and 10B face each other. The β axis extends in the direction of the pathway 1A. The γ axis extends in the (upper) vertical direction. The positive directions of the α axis, the β axis, and the γ axis are illustrated in the figures.

For example, the sizes of the parts (elements) illustrated in FIGS. 1A through 1C are as follows. As illustrated in FIG. 1A, the width of the pathway 1A between the server racks 10A and 10B is 1.4 m. In the server racks 10A and 10B, there are opening sections 10A1 and 10B1, respectively, on their pathway 1A side, so that blade-type servers can be set (inserted) in the opening sections 10A1 and 10B1.

The depth of the server racks 10A and 10B (i.e., the width of the server racks 10A and 10B in the α direction) is 1 m. On the side opposite to the opening sections 10A1 and 10B1 of the server racks 10A and 10B, there are provided respective exhaust openings to transfer heat from the servers. Due to the sizes, the distance between the exhaust opening of the server rack 10A and the exhaust opening of the server rack 10B is 3.4 m. Further, the height of the server racks 10A and 10B is 2 m.

As illustrated in FIGS. 1A and 1B, the server racks 10A and 10B are arranged parallel to each other in a manner such that the opening sections 10A1 and 10B1 of the server racks 10A and 10B face each other across the pathway 1A. Here, 30 server rack 10A and 30 server racks 10B are arranged along the pathway 1A.

As illustrated in FIG. 1C, the height of the room of the data center 1 is 3 m. The monitoring camera 20 is installed at the position which is separated on the most negative direction side in the β direction from the server racks 10A and 10B by 1.5 m, and separated on the lower side in the γ direction from the ceiling 1C by 0.5 m. Further, the installed monitoring camera 20 is separated in the β direction from the server racks 10A and 10B disposed on the most positive side in the β direction by 20 m.

Again, those sizes described above are an example only. That is, the sizes may be less than the respective sizes, or may be greater than the respective sizes.

Here, in a case where the monitoring camera 20 having the following specifications is used, the captured imaging range of the image depicting the server racks 10A and 10B which are most separated from the monitoring camera 20 is given as follows:

Imaging element (image sensing device): ⅓ inches (4.8 mm×3.6 mm), SXGA (1280×1024)

Focal length: 2.8 to 10 mm

Horizontal angle of view: 27.7 to 100.3 degrees

Vertical angle of view: 20.8 to 73.6 degrees

In a case where such a 1.3 million-pixel monitoring camera 20 is used, the imaging range per pixel at the 20 m position (the farthest position) in the mode where focal length is 10 mm is calculated as 20 (m)×0.1815 (rad)÷(1024 (pixel)÷2)≈0.007 (m/pixel), which is approximately 7 mm.

For example, a case is considered where the inclination of the optical axis occurs due to temperature change or fine vibration so that the position of the monitoring camera 20 is displaced by approximately 0.1 mm in the β axis direction. Based on the calculation using the above magnification relationship, 3.63 m at the farthest 20 m position corresponds to 1.8 mm at the position of the monitoring camera 20. Therefore, the displacement of 0.1 mm of the monitoring camera 20 corresponds to the displacement of 0.1×3.63 m/1.8 mm≈200 mm (approximately 20 cm).

FIG. 2 illustrates labels 30A, 30B, and 30C which are used in the management system according to the first embodiment.

The label 30A of FIG. 2A includes a resin sheet 30A1 having a rectangular strip shape. On one side of the sheet 30A1, eight indicators 31A are arranged which indicate the temperature. The label 30A further includes markers 32A and 32B which are disposed on the respective ends of the eight indicators 31A. The part of the surface of the sheet 30A1 other than the parts of the eight indicators 31A and the markers 32A and 32B is covered with a black film (mask).

The eight indicators 31A use the characteristics of "selective reflection" by the cholesteric liquid crystal, and are the cholesteric liquid crystals having different stages of the temperature ranges to create green color. Those eight cholesteric liquid crystals are arranged in one line with appropriate shift from each other on the surface of the sheet 30A1. The indicators 31A are an example of the "display part".

The temperature of the environment where the label 30A is disposed is indicated by filling the sections of the eight indicators 31A with respective liquid crystals so that the figures (temperature values), which comes out green in accordance with the respective temperature ranges, can be displayed to emerge on the surface of the sheet 30A1 or by arranging so that the figures (temperature values) can come out in color (the figures can emerge) by covering the surface of the sheet 30A1, all of whose sections are filled with the respective liquid crystals, with a black mask. The "selective reflection" is a reversible reaction, so that it is possible to use the characteristics of the "selective reflection" in a repetitive manner.

The eight indicators 31A are arranged to be displayed as "18° C.", "20° C.", "22° C.", "24° C.", "26° C.", "28° C.", "30° C.", and "32° C.", respectively. Originally, the label 30A is to be displayed in color. To that end, for example, when the environment temperature is 24° C., the indicator 31A of "24° C." comes out green, three indicators 31A of "18° C.", "20° C.", and "22° C." come out in pale blue (generate weak blue light), and four indicators 31A of "26° C.", "28° C.", "30° C.", and "32° C." do not generate color. In this case, the figures of the four temperatures "26° C.", "28° C.", "30° C.", and "32° C." are not displayed due to the black film of the sheet 30A1.

Further, for example, in a case where the environmental temperature is 25° C., which cannot be (directly) displayed with the eight indicators 31A, two temperatures (figures), which are closer to the environmental temperature than any other temperatures, come out in pale green (generate weak green light). That is, when the environmental temperature is 25° C., only two indicators 31A of "24° C." and "26° C." come out in pale green (generate weak green light).

The markers 32A and 32B are provided so that both ends of the label 30A can be recognized (detected) in the imaging process described below. The upper marker 32A and the lower marker 32B have different white L-shaped patterns.

For example, the markers 32A and 32B are square-shaped red sections on the center of which the respective white L-shaped patterns are formed. To form such markers 32A and 32B, for example, red retroreflective ink or phosphorescent ink is applied to the sheet 30A1 to form the square-shaped red sections and then, the respective white L-shaped patterns are formed on the center of the square-shaped red sections.

The white L-shaped patterns may be formed by applying while retroreflective ink or phosphorescent ink. However, when the sheet 30A1 is white, the white L-shaped patterns may be formed as the regions to which the red retroreflective ink or phosphorescent ink is not applied.

The label 30B of FIG. 2B includes a resin sheet 30B1 having a rectangular strip shape. On one side of the sheet 30B1, eleven indicators 31B, which indicate the temperatures from "12° C." to "32° C.", are arranged. The label 30B further includes the markers 32A and 32B which are disposed on the respective ends of the eleven indicators 31B. The part of the surface of the sheet 30B1 other than the parts of the eleven indicators 31B and the markers 32A and 32B is covered with a black film (mask).

The label 30B of FIG. 2B is, basically, similar to the label 30A of FIG. 2A except the number of indicators and the directions of the figures.

The label 30C of FIG. 2C differs from the label 30A of FIG. 2A and the label 30B of FIG. 2B in that the label 30C indicates environmental humidity. The label 30C of FIG. 2C includes a resin sheet 30C1 having a rectangular strip shape. On one side of the sheet 30C1, seven indicators 31C, which indicate the humidity from "10%" to "70%", are arranged. The label 30C further includes the markers 32A and 32B which are disposed on the respective ends of the seven indicators 31C. The part of the surface of the sheet 30C1 other than the parts of the seven indicators 31C and the markers 32A and 32B is covered with a white film (mask).

For example, the seven indicators 31C are formed by using the mechanism that cobalt chloride is impregnated in a blotting paper, so that cobalt chloride in the blotting paper generates (changes) colors depending on the relative humidity of a predetermined level. The color of the indicators 31C is returned to the original color when the relative humidity is lower than the predetermined level. The seven indicators 31C are set (formed) so as to have the respective relative humidities, which differ from each other, to generate (change) colors. Specifically, the seven indicators 31C are set (formed) so as to generate (change) colors at the respective environmental humidities "10%", "20%", "30%", "40%", "50%", "60%", and "70%".

The indicators 31C of the label 30C come out in blue when the environmental humidity exceeds the respective humidities which are allocated to the indicators 31C. On the other hand, indicators 31C of the label 30C come out in pink when the environmental humidity is lower than the respective humidities which are allocated to the indicators 31C.

In the management system according to the first embodiment, a plurality of labels such as the labels 30A, 30B, and 30C are placed on the server racks 10A and 10B. Further, the image including the labels is obtained (captured) by the monitoring camera 20 and image processing is performed on the image, so that the temperature or the humidity, which is displayed by each of the labels, is detected.

In order to make it possible to read the indicators 31A through 31C and the markers 32A and 32B by such image processing, it is desired that the image has sufficient number of pixels so as to recognize (detect) whether each of the indicators 31A through 31C comes out in color in the image data and also that the markers 32A and 32B can be recognized.

That is, it is desired to, for example, set the sizes of the indicators 31A through 31C and the markers 32A and 32B, determine the specifications such as resolution of the monitoring camera 20, and set the distance to the position (point) which is the farthest from the monitoring camera 20 in capturing images, so that the indicators 31A through 31C and the markers 32A and 32B can be recognized. Details of the content are described below.

Further, FIGS. 2A through 2C illustrates labels 30A through 30C, respectively, which indicate the environmental temperature or the environmental humidity by using liquid crystal. Note that, however, in place of the thermal label using a liquid crystal, for example, a thermal label having an indicator using the change of the degree of the transparency depending on the temperature of the thermosensitive body may be used. The indicator of such thermal label changes its color shade (color) depending on whether the temperature is higher or lower than the threshold temperature. For example, there is an indicator of the thermal label which comes out in dark brown purple color when the temperature is lower than the threshold temperature, and comes out in yellow-tinged bright red color when the temperature is higher than or equal to the threshold temperature. Further, there is an indicator of the thermal label which comes out in yellow-tinged bright orange color when the temperature is lower than the threshold temperature, and comes out in yellow color when the temperature is higher than or equal to the threshold temperature. Further, there is there is an indicator of the thermal label which comes out in reddish orange color when the temperature is lower than the threshold temperature, and comes out in reddish yellow color when the temperature is higher than or equal to the threshold temperature.

FIG. 3 illustrates a management system 100 according to the first embodiment.

Figure 3A:
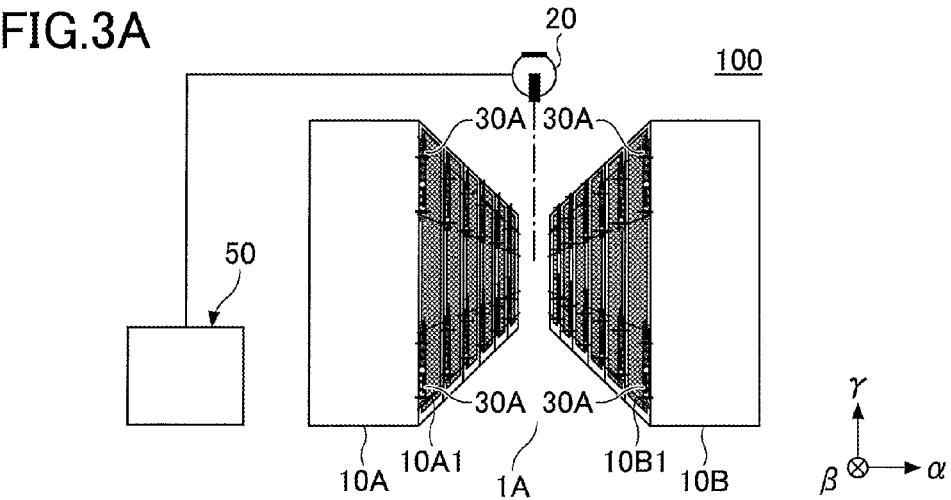
FIG. 3A illustrates a management system 100 according to the first embodiment.
Figure 3B:
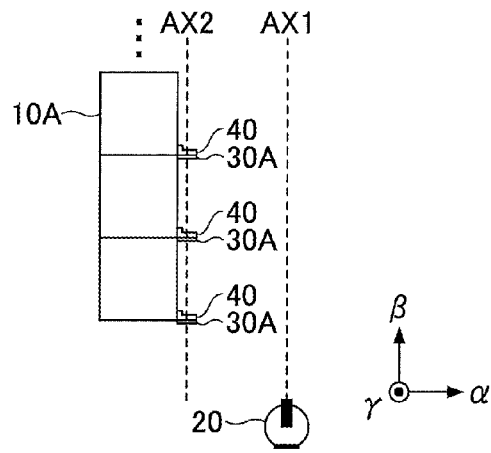
FIG. 3B illustrates the management system 100 according to the first embodiment.
Figure 3C:
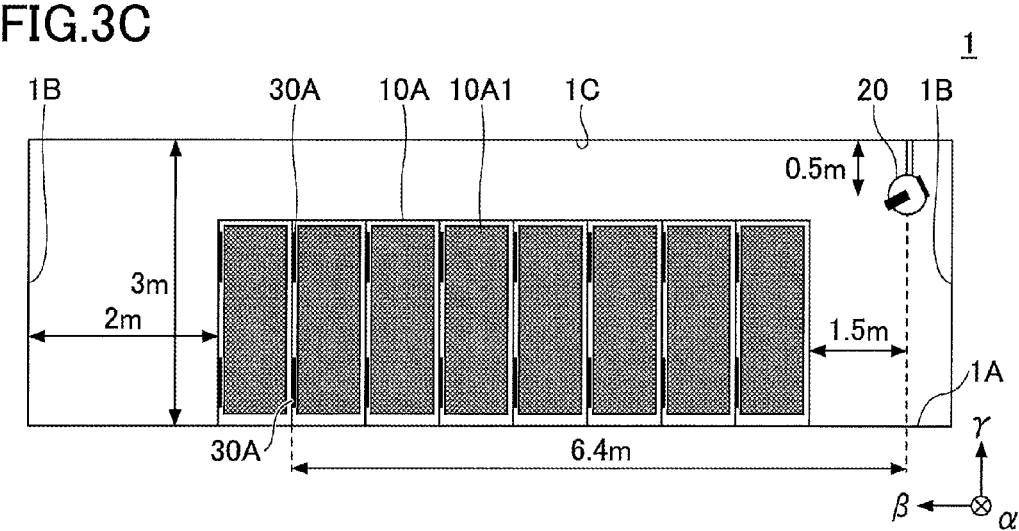
FIG. 3C illustrates the management system 100 according to the first embodiment.

The management system 100 includes the monitoring camera 20, the labels 30A, and a control apparatus 50. FIG. 3A illustrates the layout of the server racks 10A and 10B which are arranged along the pathway 1A. FIG. 3B illustrates the positional relationship between the monitoring camera 20 and the labels 30A seen in a plan view. FIG. 3C illustrates the eight server racks 10A seen from the pathway 1A side. Similar to FIGS. 1A through 1C, in FIGS. 3A through 3C, the αβγ coordinate system is defined.

FIG. 3A illustrates eight server racks 10A and eight server racks 10B. On each of the server racks 10A and 10B, two labels 30A are mounted. The label 30A is the same as the label 30A of FIG. 2A. On each of the eight server racks 10A and the eight server racks 10B, the label 30A is mounted on each of upper and lower sides of the side wall which is disposed on the negative β axis direction side relative to the corresponding opening sections 10A1 and 10B1 facing the pathway 1A (see FIG. 3).

The position of the upper end of the upper label 30 in the height direction (γ axis direction) corresponds to the upper end of the server racks 10A and 10B. On the other hand, the upper end of the lower label 30 in the height direction (γ axis direction) is positioned at the level which is higher than the floor surface of the pathway 1A by 0.5 m.

All the labels 30 protrude from the server racks 10A and 10B to the pathway 1A side, and are mounted in a manner such that the labels 30 are parallel to the ay plane and face the negative β axis direction side. That is, the labels 30 include respective indicators 31A (display part) whose coloring positions change depending on the temperature level. Further, the labels 30 are mounted at the positions different from each other in the direction separating from the monitoring camera 20. Further, the direction where the coloring position changes in each of the labels 30 is different from the direction separating from the monitoring camera 20.

In order to mount the labels 30A on the server racks 10A and 10B as described above, for example, a plate-shaped plate-like member 40 having a surface whose size is the same as that of the label 30 (see FIG. 3B) is mounted on each of upper and lower sides of the side wall which is disposed on the negative β axis direction side of each of the corresponding opening sections 10A1 and 10B1. Then, the labels are placed on the surface on the negative β axis direction side of the respective plate-like members 40.

FIG. 3B illustrates the optical axis ΔXI of the monitoring camera 20 and the axis ΔX2 which also corresponds to the normal line of the labels 30 mounted on the server racks 10A. The optical axis ΔXI is parallel to the axis ΔX2.

Further, FIG. 3C illustrates the state where the labels 30 are mounted on the eight server racks 10A when viewed from the pathway 1A side.

As illustrated in FIG. 5C, the distance in the β axis direction between the label 30A, which is mounted on the server rack 10A disposed at the position which is on the most positive direction side among the positions in the β axis direction of the eight server racks 10A, (i.e., the most farthest label 10A from the monitoring camera 20) and the monitoring camera 20 is 6.4 m. This is because the width in the β axis direction of a single server rack 10A is 0.7 m and the distance in the β axis direction between the server rack 10A, which is the closest to the monitoring camera 20 among the eight server racks 10A, and the monitoring camera 20 is 1.5 m.

Here, similar to the case which is described with reference to FIG. 1, a case is considered where the image of the farthest label 30A is captured by the monitoring camera 20 which has 1.3 million pixels.

When the focal length of the monitoring camera 20 is set to 2.8 mm and the image is captured, the view in the vertical direction and in the horizontal direction relative to the label 30A which is closest to the monitoring camera 20 is calculated as follows.

$$\text{View in vertical direction: } 1.6 \text{ m} \times 0.875 \times 2 = \pm 1.4 \text{ m} \quad \text{Formula (1)}$$

$$\text{View in horizontal direction: } 1.6 \text{ m} \times 0.642 \times 2 = \pm 1 \text{ m} \quad \text{Formula (2)}$$

Here, the view in the vertical direction is understood by assuming that the angle of view extends in the horizontal direction, and the view in the horizontal direction is treated by assuming that the angle of view extends in the vertical direction.

Further, the value "1.6 m" in Formulas (1) and (2) is the distance between the monitoring camera 20 and the label 30A which is the closest to the monitoring camera 20. Further, the value "0.875" in Formula (1) refers to half of the value in radians which is converted from the horizontal angle of view 100.3°.

Further, the value "0.642" in Formula (2) refers to half of the value in radians which is converted from the vertical angle of view 73.6°.

Further, in a case where the focal length of the monitoring camera 20 is set to 2.8 mm, the sizes which occupy one pixel in an image in the vertical direction and in the horizontal direction at the position of the label 30A, which is the farthest from the monitoring camera 20, are described below. Here, it is assumed that the position of the label 30A, which is the farthest from the monitoring camera 20, corresponds to the position which is separated from the monitoring camera 20 by 6.4 m.

Size of one pixel in vertical direction: 6.4 m×0.875 rad÷(1280 pixels÷2)≈8.8 mm/pixel      Formula (3)

Size of one pixel in horizontal direction: 6.4 m×0.642 rad÷(1024 pixels÷2)≈8 mm/pixel      Formula (4)

Figure 4:
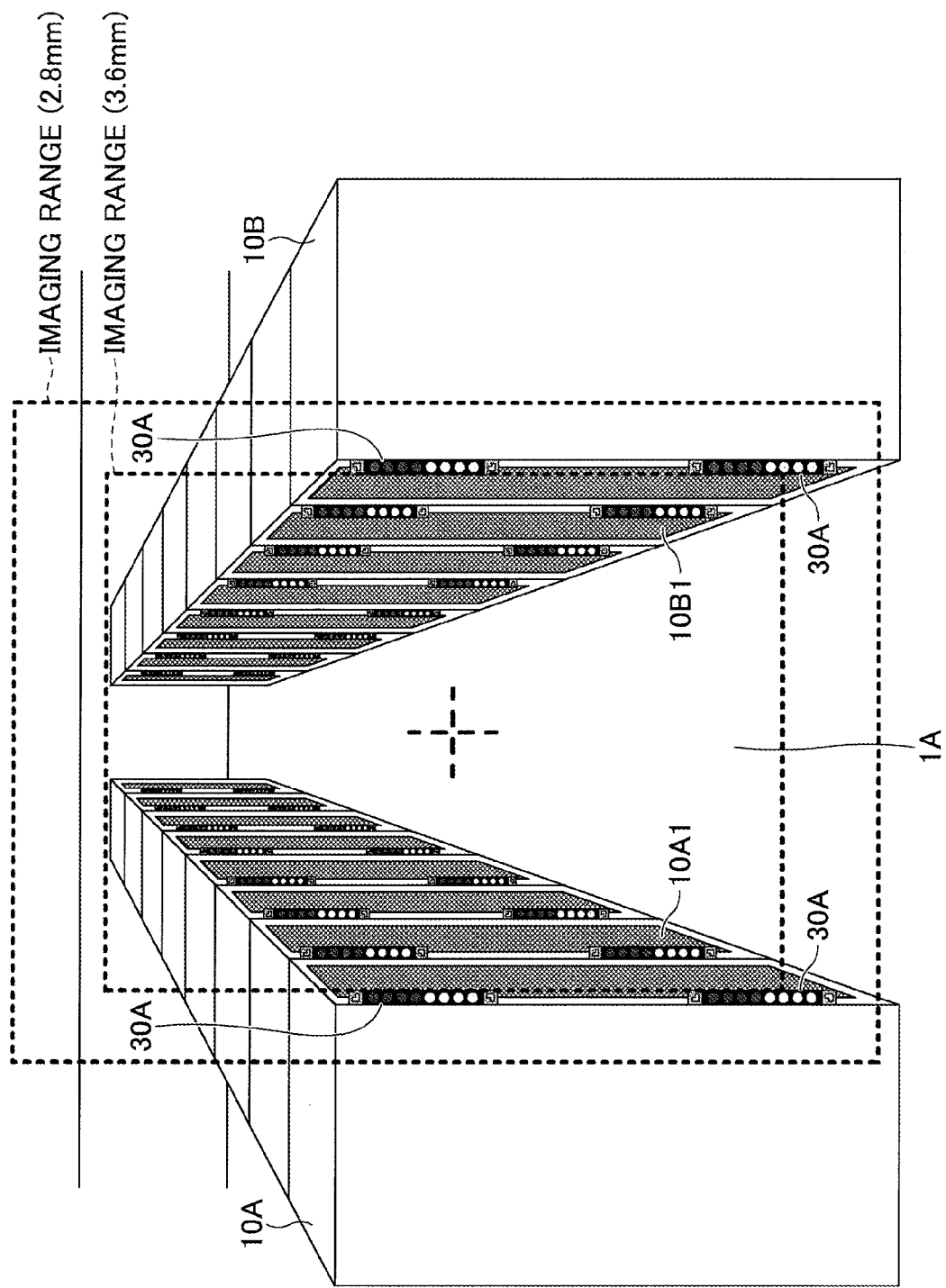
FIG. 4 illustrates an image which is captured and obtained by a monitoring camera 20.

FIG. 4 illustrates an example image captured by the monitoring camera 20.

In FIG. 4, the cross line indicates the focus orientation (focal point orientation), and two dotted rectangular frames indicate the imaging ranges when the focal length is 2.8 mm and 3.6 mm. In the imaging range where the focal length is 2.8 mm, it is possible to capture the images of all 32 labels 30A. On the other hand, in the imaging range where the focal length is 3.6 mm, although it is not possible to completely capture the image of four labels 30A which are the nearest to the monitoring camera 20 among the 32 labels 30A, it is possible to capture the farthest labels 30A with higher resolution.

Due to this, in order to maintain the resolution of the image of the labels 30A in the back side, the focal length may be changed between the front side and the back side.

In the image when the focal length is 3.6 mm, the sizes in the vertical direction and in the horizontal direction at the position of the labels 30A which is the farthest from the monitoring camera 20 are obtained by using the focal length as described below.

Size in vertical direction of one pixel: 2.8÷3.6× 8.8≈6.8 mm/pixel      Formula (5)

Size in horizontal direction of one pixel: 2.8÷3.6× 8≈6.2 mm/pixel      Formula (6)

As described, in the image when the focal length is 3.6 mm, the resolution can be improved by 20% when compared with the image when the focal length is 2.8 mm.

Based on the values obtained by Formulas (1) through (4), the sizes of the indicators 31A and markers 32A and 32B of the farthest labels 30A are considered.

When approximately 9 pixels (=3 pixels (vertical)×3 pixels (horizontal)) can be secured for each of the indicators 31A and markers 32A and 32B, the indicators 31A and markers 32A and 32B can be sufficiently recognized in the image processing. Therefore, the size in each of the vertical and horizontal directions of the indicators 31A and markers 32A and 32B is approximately 18 mm at minimum.

Based on the above, regarding the sizes of the labels 30A, for example, the length of the indicator 31A in the vertical and horizontal directions is set to 20 mm, and the length of each of the markers 32A and 32B in the vertical and horizontal directions is set to 30 mm.

Further, in a case where the signal-to-noise (S/N) ratio is relatively high at the label 30A in the captured image of the label 30A, when it is still possible to recognize each of the indicators 31A and markers 32A and 32B with the number of pixels less than 9 pixels, it is possible to reduce the lengths in the vertical and horizontal directions. For example, when each of the indicators 31A and markers 32A and 32B can be recognized with 4 pixels (=2 pixels (vertical)×2 pixels (horizontal), it is possible to further reduce the sizes of the labels 30A.

Next, a computer system which is used as the control apparatus 50 of the management system 100 is described.

Figure 5:
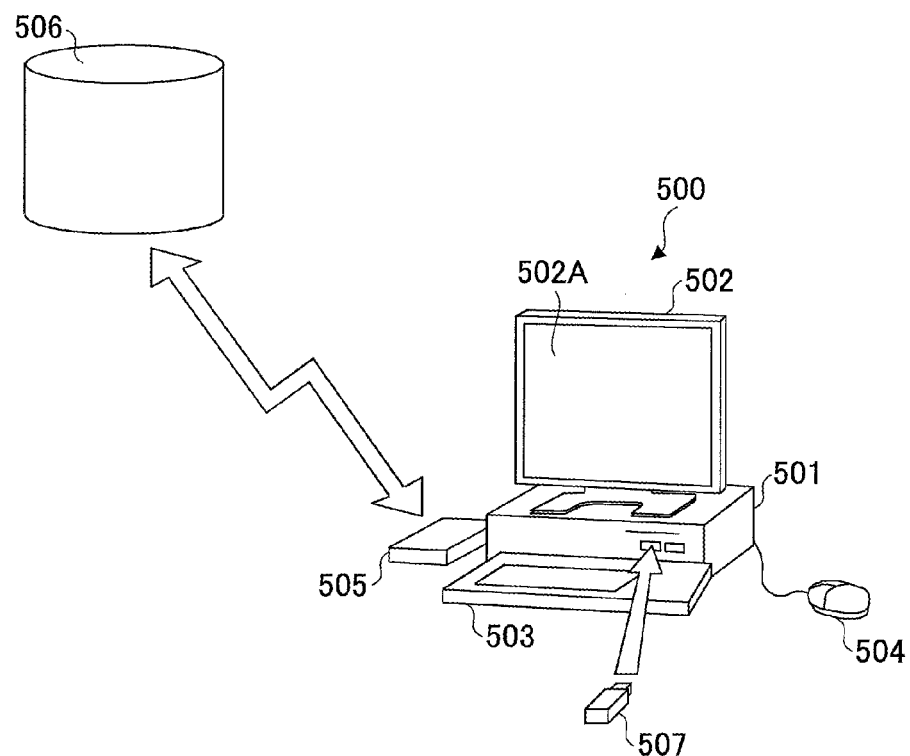
FIG. 5 is a perspective view of a computer system 500 which is used as a control apparatus 50 according to the first embodiment.

FIG. 5 is a perspective view of the computer system used as the control apparatus 50 according to the first embodiment. A computer system 500 of FIG. 5 includes a computer 501, a display 502, a keyboard 503, a mouse 504, and a modem 505.

The computer 501 includes a Central Processing Unit (CPU), a Hard Disk Drive (HDD), a Disk Drive, etc. The display 502 is a display section such as, for example, a liquid crystal monitor which displays an analysis result, etc., on a display screen 502A based on the instructions from the computer 501. The keyboard 503 in an input section to input various information in the computer system 500. The mouse 504 is an input section to designate an arbitrary position on the display screen 502A of the display 502. The modem 505 accesses an external database, etc., and downloads a program, etc., stored in an external computer system.

The program which causes the computer system 500 to function as the control apparatus 50 is stored in a portable recording medium such as a Universal Serial Bus (USB) memory 507, or is downloaded from a recording medium 506 of another computer system by using a communication apparatus such as the modem 505, so as to be input to the computer system 500 to be compiled.

The program which causes the computer system 500 to function as the control apparatus 50 causes the computer system 500 to operate as the control apparatus 50. For example, the program may be stored in a computer-readable recording medium such as a USB memory 507. Here, note that the computer-readable recording medium is not limited to a portable-type recording medium such as, for example, the USB memory 507, a Compact Disc Read Only Memory (CD-ROM), a magnetooptical disc, an IC card memory, and a magnetic disk like a floppy disk (registered trademark). Further, the computer-readable recording medium includes various recording media which are accessible in the computer system which is connected via a communication device such as the modem 505 or a Local Area Network (LAN)

Figure 6:
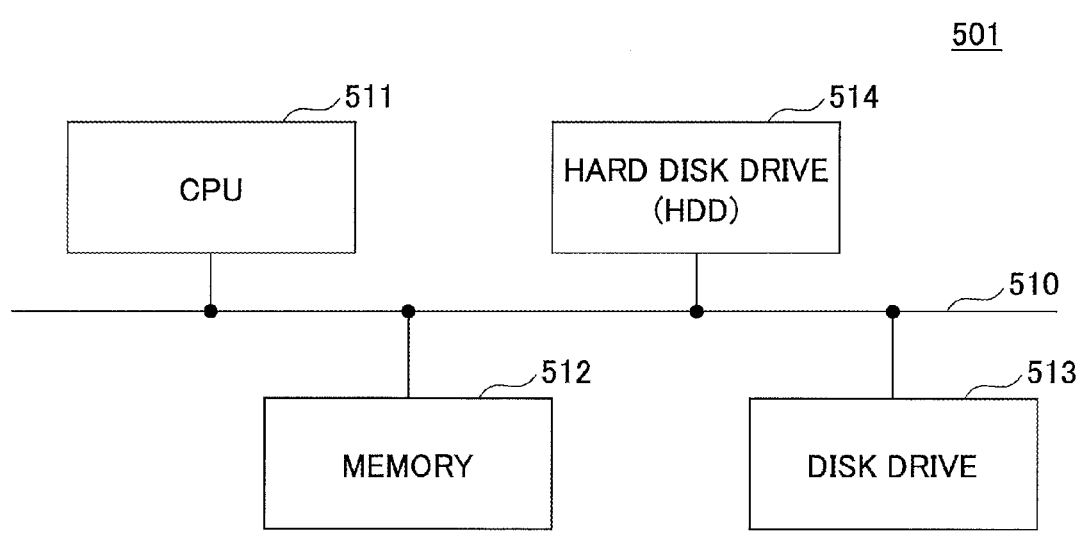
FIG. 6 illustrates an example configuration of a main part in a computer 501 of the computer system 500.

FIG. 6 illustrates an example configuration of a main part in the computer 501 of the computer system 500. The computer 501 includes the CPU 511, a memory 512, which includes a Random Access Memory (RAM), a ROM, etc., a disk drive 513 for the USB memory 507, and the HDD 514, which are connected to each other via a bus 510. In the first embodiment, the display 502, the keyboard 503, and the mouse 504 are connected to the CPU 511 via the bus 510. Note that, however, those elements may be directly connected to the CPU 511. Further, the display 502 may be connected to the CPU 511 via a known graphic interface (not shown) which performs a process on the input/output image data.

In the computer system 500, the keyboard 503 and the mouse 504 are the input section of the control apparatus 50.

The display 502 is the display section to display, for example, a selection result selected by the control apparatus 50 on the display screen 502A.

Here, note that the configuration of the computer system 500 is not limited to the configurations of FIGS. 5 and 6. For example, one or more elements may be added and alternatively used.

FIG. 7 illustrates an example of the control apparatus 50 which is included in the management system 100 according the first embodiment and example data which are used by the control apparatus 50.

Figures 7A, 7B:
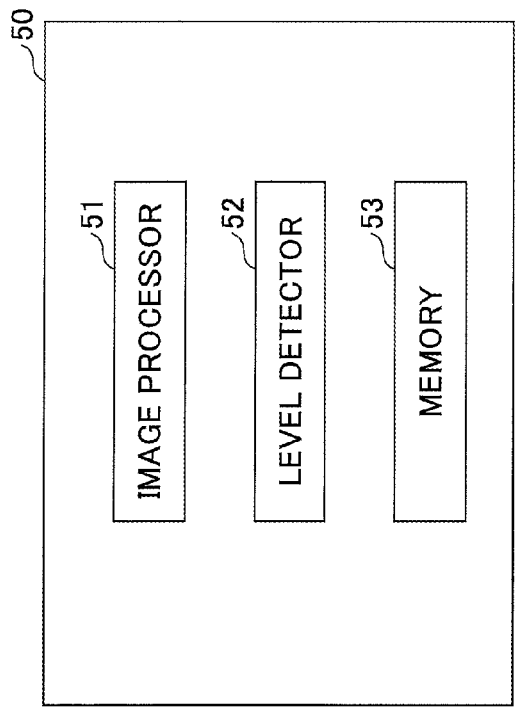
FIG. 7A illustrates the control apparatus 50 included in the management system 100 according to the first embodiment.
FIG. 7B illustrates example data which are used by the control apparatus 50.

As shown in FIG. 7A, the control apparatus 50 includes an image processor 51, a level detector 52, and a memory 53. The control apparatus 50 is connected to the monitoring camera 20, so that based on the image data output from the monitoring camera 20, the control apparatus 50 detects a temperature distribution of 32 labels 30A.

The image processor 51 performs a warping process based on, for example, an image transformation (conversion) process using a perspective projection transformation, and outputs the processed image data to the level detector 52. In the image data, the number of pixels of the image indicating the label 30A which is near the monitoring camera 20 is decreased as the distance between the label 30A and the monitoring camera 20 is increased. In order to automatically calculate (obtain) the temperature based on the image data, it is desired to perform a process which is based on a predetermined rule. However, the number of pixels expressing the label 30A varies depending on the distances between the label 30A and the monitoring camera 20 although the same labels 30 are used. Therefore, it is difficult to apply (set) a (same) rule to the control apparatus 50. By performing the warping process, the number of the pixels in the images of the labels 30A is unified, so that it becomes possible for the control apparatus 50 to perform automatic calculation which is described below. Here, the warping process is an example of the first image processing.

That is, the warping process, which is an example of the first image processing, refers to a process which transforms (converts) the image data in a manner such that the difference in the number of pixels expressing the labels 30A among a plurality of labels 30A included in the image data which have been transformed is less than the difference in the number of pixels expressing the labels 30A among the labels 30A included in the image data which has not been transformed.

In other words, the image processor 51 performs the first image processing so that the number of pixels expressing the image of each of the plurality of labels 30A equal to each other among the plurality of labels 30A by transforming the image data in a manner such that, when comparing the image of the plurality of indicators 31A before the first image processing is performed with the image of the plurality of indicators 31A after the first image processing is performed, not only the distance between the marker 32A and the marker 32B in each of the plurality of labels 30A in the image becomes equal to (is similar to) each other among the plurality of labels 30A but also the ratio of the distances between a pair of the markers 32A and 32B and another pair of the markers 32A and 32B of the labels 30A adjacent to each other in the plurality of labels 30A becomes equal to (is similar to) the ratio thereof in actual space.

Here, a case is described where the image processor 51 performs the image transformation process using the perspective projection transformation as one example of the warping process. Note that, however, the warping process, which is performed by the image processor 51, is not limited to the linear image transformation process such as the perspective projection transformation. For example, a non-linear image transformation process may alternatively be used. Specific content of the warping process is described below.

The level detector 52 scans the image of the indicators 31A, on which the image processing has been performed by the image processor 51, along the arranging direction of the indicators 31A, and detects the temperature distribution based on the color distribution of the indicators 31A. The level detector 52 detects the level of the temperature based on the luminance information of the pixels corresponding the indicators 31A.

The memory 53 stores the image data expressing the image of the labels 30A and the data indicating the distances between the labels 30A. An example structure of the data is illustrated in FIG. 7B.

As illustrated in FIG. 7B, the image data of the labels 30A include a positional relationship between the labels 30A, a shape and color of the sheet 30A1, a shape and position of eight indicators 31A, and a shape, color, and position of the markers 32A and 32B. The data indicating the positional relationship between the labels 30A refer to the distances between the labels 31A in the in the β axis direction. Further, the data indicating the positional relationship between the labels 30A may be the data indicating the coordinates of the labels 30A in the αβγ coordinate system. Further, the data indicating the distances (gaps) between the labels 30A is X mm.

FIG. 8 is an example flowchart of the process performed by the control apparatus 50 of the management system 100.

First, the control apparatus 50 detects 32 labels 30A mounted on server racks 10A and 10B and the markers 32A and 32B of the labels 30A (step S1). The process in step S1 is performed by the image processor 51 of the control apparatus 50.

The image processor 51 detects the labels 30A and the markers 32A and 32B by performing pattern matching (template matching) based on the image data of the label 30A stored in the memory 53.

Next, the control apparatus 50 extracts an image which is included in a region which is defined by 16 labels 30A included in the server rack 10A and a region which is defined by 16 labels included in the server rack 10B, and performs the warping process on the extracted image (step S2). The process in step S2 is performed by the image processor 51 of the control apparatus 50.

As the warping process, for example, an image transformation process using the perspective projection transformation is performed. The image on which the warping process has been performed in step S2 includes the labels 30A which are detected in step S1 and the markers 32A and 32B of the labels 30A.

The image processor 51 performs the process of transforming the data, which indicate the distance (X mm) between the labels 30A stored in the memory 53, into the data which indicate the distance (ΔX mm) between the labels 30A in the image on which the warping process has been performed in step S2. To that end, for example, the data representing the distance (X mm) may be transformed into the data representing the distance (ΔX mm) by using a determinant which is used in transforming the coordinates included in the image in the warping process.

Next, the control apparatus 50 scans the image along the scanning line which is connected between the markers 32A and 32B with respect to each of the labels 30A included in the image on which the warping process has been performed in step S2 (step S3). The process in step S3 is performed by the level detector 52 of the control apparatus 50.

As described, it is desired to determine in advance the scanning direction of the scanning performed along the scanning line with respect to each of the labels 30A. This is to unify the reading directions of the labels 30A. For example, the scanning may be performed in the direction from the lower marker 32B to the upper marker 32A (in the upward direction). By performing the scanning in this way, it becomes possible to continuously read from the indicator on the lower temperature side to the indicator on the upper temperature side.

Further, the control apparatus 50 detects a distribution of the temperatures (temperature distribution) based on the distribution of colors of the indicators 31A which is read in step S3. The process in step S4 is performed by the level detector 52 of the control apparatus 50.

Next, details of the processing performed by the control apparatus 50 having the configuration as described above are described.

Figure 9:
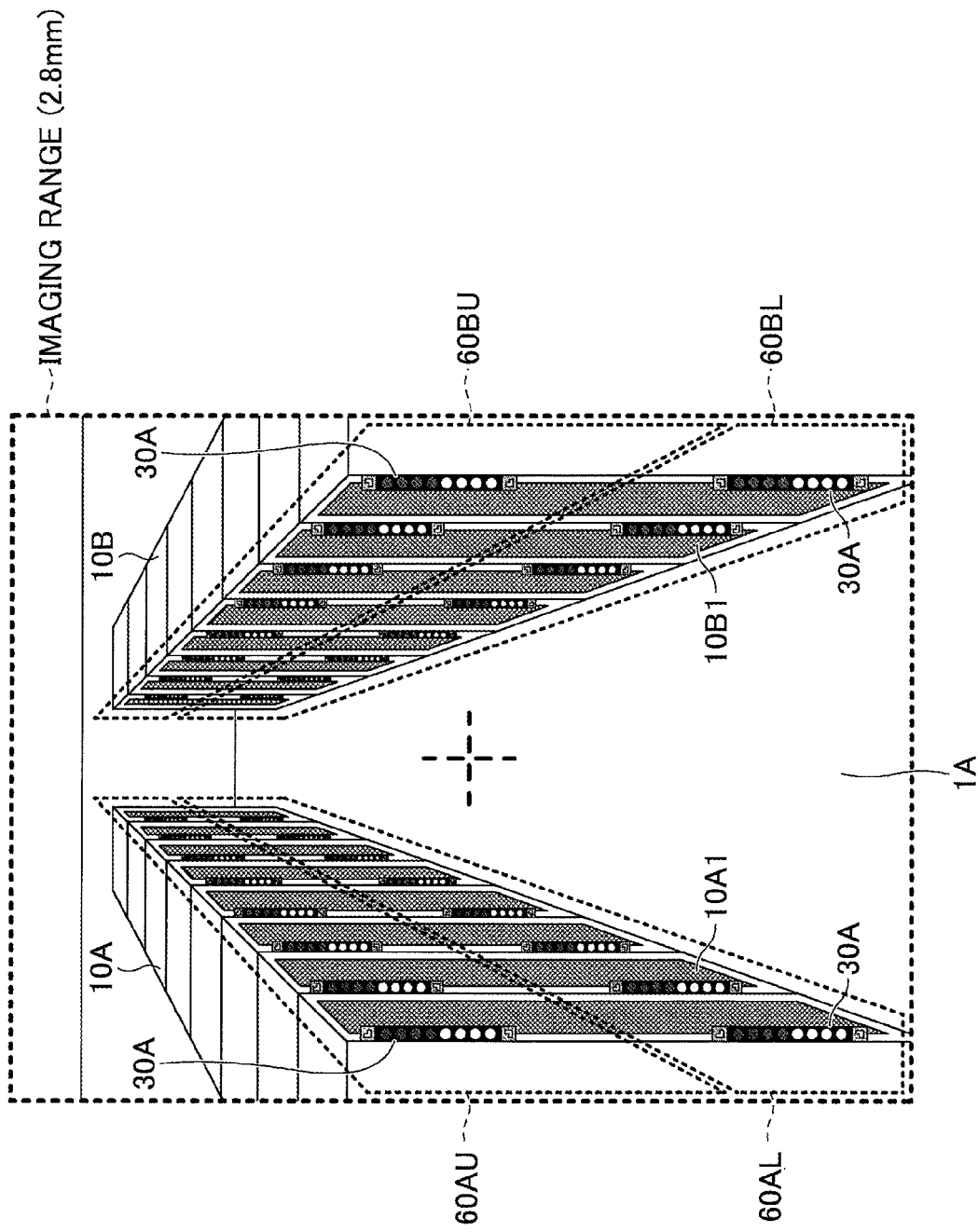
FIG. 9 illustrates an example image which is extracted by the control apparatus 50.

FIG. 9 illustrates an example of the image which is extracted by the control apparatus 50.

The image of FIG. 9 is based on the imaging range which is obtained (captured) by setting the focal length of the monitoring camera 20 to 2.8 mm. The cross line indicates the focus orientation of the monitoring camera 20.

The image processor 51 of the control apparatus 50 sets regions 60AU, 60AL, 60BU, and 60BL based on the positions in the image of the labels 30A which are detected by the pattern matching. The regions 60AU, 60AL, 60BU, and 60BL are regions to be searched in order to search for the markers 32A and 32B.

The region 60AU includes eight labels on the upper side of the server rack 10A. The region 60AL includes eight labels on the lower side of the server rack 10A. The region 60BU includes eight labels on the upper side of the server rack 10B. The region 60BL includes eight labels on the lower side of the server rack 10B.

FIG. 10 illustrates a state when a process is performed on the region 60AU. FIG. 11 illustrates a state of the warping process. There, the region 60AU is exemplarily described. Note that the description is similar to the regions 60AL, 60BU, and 60BL as well.

FIG. 10A illustrates the server rack 10A and the region 60AU of FIG. 9. For simplification purposes, only six racks in the middle are illustrated (that is, the racks in both ends are not illustrated). Note that, however, the processing method, functions, and effects are not changed due to the simplification. The image processor 51 detects the labels 30A and the markers 32A and 32B by performing the pattern matching within (with respect to) the region 60AU. To distinguish the markers 32A and 32B one from another, for example, the directions of the white L-shaped patterns in the center of the square-shaped red sections may be recognized (determined) by using a region for determination which is smaller than the pixel region which is occupied by the markers 32A and 32B included in the farthest label 30A in the image.

For example, in a case where the pixel region which is occupied by the markers 32A and 32B of the farthest 30A corresponds to the region of 9 pixels (=3 pixels (vertical)×3 pixels (horizontal), for example, the region for determination may be the region corresponding to only one pixel or the region of 4 pixels (=2 pixels (vertical)×2 pixels (horizontal).

Here, in the detection of the labels 30A and the markers 32A and 32B by pattern matching, for example, the process using the following normalized cross-correlation coefficient is performed.

With respect to each of the labels 30A and the markers 32A and 32B, coordinates where the correlation is higher than a certain value are extracted. In the method of acquiring the correlation, for example, the normalized cross-correlation coefficient (R_NCC) of Formula (7) is used.

$$R\_NCC = \frac{\sum_{j=0}^{N-1} \sum_{i=0}^{M-1} I(i,j)T(i,j)}{\sqrt{\sum_{j=0}^{N-1} \sum_{i=0}^{M-1} I(i,j)^2 \times \sum_{j=0}^{N-1} \sum_{i=0}^{M-1} T(i,j)^2}} \quad \text{Formula (7)}$$

In Formula (7), "I" denotes the luminance value obtained in the region for determination, "T" denotes the luminance value of the image of the markers 32A and 32B, and "i" and "j" denote the coordinates in the image.

The normalized cross-correlation coefficient (R_NCC) refers to a formula which normalizes the integrated value between the luminance values of the coordinates of the extracted images of the region for determination which are extracted from the image and the luminance values of the coordinates of the images of the markers 32A and 32B which are for the pattern matching. The maximum value of the normalized cross-correlation coefficient (R_NCC) is one.

The luminance value obtained as described above is obtained for each of RGB colors. For example, when the center coordinates of a region for determination is set as first coordinates, it is assumed that all the luminance values of the RGB colors of the first coordinates of the image are less than 0.2. Further, when the center coordinates of a region for determination are set as second coordinates, it is assumed that all the luminance values of the RGB colors of the second coordinates of the image are greater than or equal to 0.5. In this case, it is determined that no correlation is obtained with respect to the first coordinates and a correlation is obtained with respect to the second coordinates. Further, the second coordinates, which have been determined to have the correlation, are treated so that the pattern has been matched.

By performing the process as described above, the labels 30A and the markers 32A and 32B are detected as illustrated in FIG. 10B.

Next, as illustrated in FIG. 10C, a straight line which passes through the eight markers 32A included in the respective eight labels 30A is set. Similarly, another straight line which passes through the eight markers 32B included in the respective eight labels 30A is set.

Figure 11A:
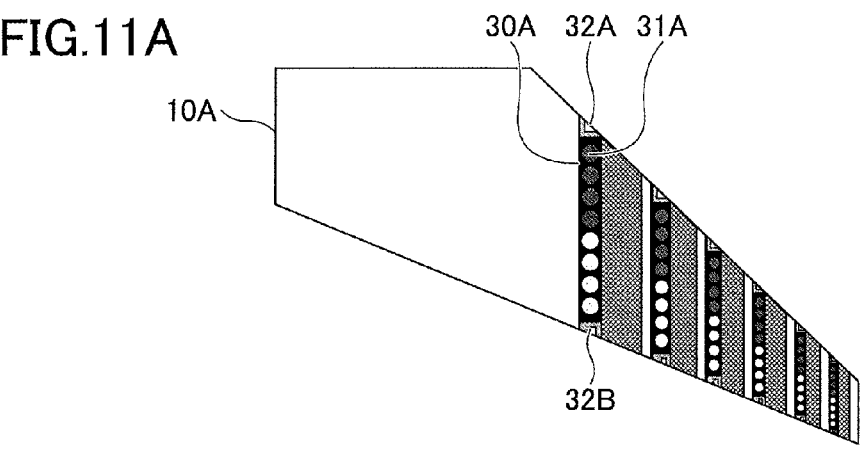
FIG. 11A illustrates an example state of a warping process.

Next, the image processor 51 cuts out the area where the region between the two straight lines of FIG. 10A overlaps with the region 60AU. As a result of this process, an image as illustrated in FIG. 11A is obtained. In this example, an image is described where the six labels 30A which correspond to the six labels 30A in FIG. 10 are cut out. Note that, however, the same processing is used and the same effects can be obtained when the image is used where one more rack on the front side and one more rack on the back side are additionally included.

In the image of FIG. 11A, due to the positional difference of the eight labels 30A in the depth direction (in the β direction in FIG. 3), the image of the label 30A become smaller and obliquely shifted on the right lower side towards the vanishing point as the position of the label 30 becomes farther (to the right side in FIG. 11A).

Figure 11B:
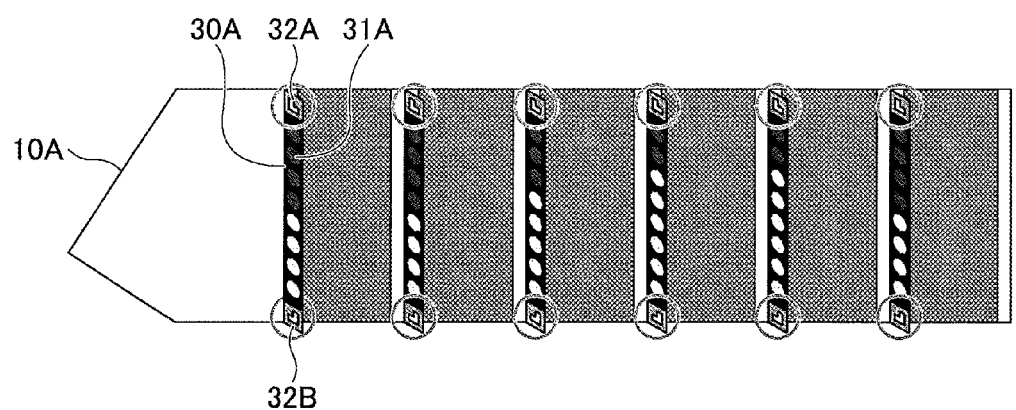
FIG. 11B illustrates an example state of the warping process.

Next, the image processor 51 performs the warping process, which is based on the image transformation process using, for example, the perspective projection transformation, on the image of FIG. 11A, and obtains the image of FIG. 11B. In the image of FIG. 11A, the number of pixels in the image corresponding to the label 30A closer to the monitoring camera 20 among the eight labels 30A is more than four times greater than that corresponding to the label 30A farther from the monitoring camera 20. On the other hand, in the image of FIG. 11B, the number of pixels in the image corresponding to the label 30A closer to the monitoring camera 20 among the six labels 30A is substantially equal to that corresponding to the label 30A farther from the monitoring camera 20. As a result, the positions of the eight labels 30A in the depth direction (in the $\beta$ direction in FIG. 3) are arranged in place (with substantially equal intervals).

Further, in the image of FIG. 11B, the shape of the label 30A is a parallelogram where the right side is lower than the left side. This is because rotational transfer is carried out in order to arrange the positions of the eight labels 30A in the image of FIG. 11A in place in the up-and-down direction. Further, in FIG. 11A, each of the markers 32A and 32B is surrounded with a gray circle.

Figure 11C:
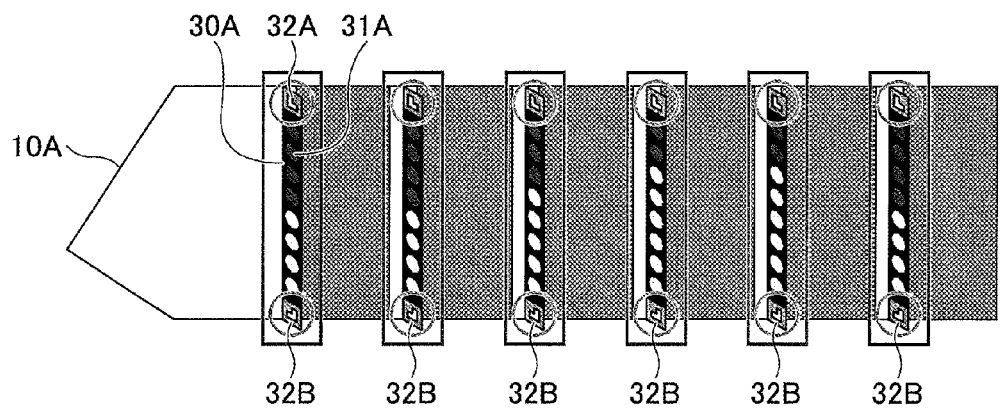
FIG. 11C illustrates an example state of the warping process.

Next, as illustrated in FIG. 11C, in each of the labels 30A, the image processor 51 sets a scanning line which is connected between the center of the label 32A and the center of the label 32B. In FIG. 11C, for explanatory purposes, the scanning line is depicted as the gray frame which surrounds each of the labels 30A. Note that, however, the (practical) scanning line refers to the straight line connecting the center of the marker 32A and the center of the 32B in each of the labels 30A. The scanning line is used to scan the images of the indicators 31A disposed between the marker 32A and the center of the 32B in each of the labels 30A.

In setting the scanning line, first, the eight markers 32A and the eight markers 32B are divided into eight groups.

In the process, for example, the signal levels of the RGB color signals of all the pixels of the image of FIG. 11B, and the left end of the server rack 10A is detected. Then, a group of the markers 32A and 32B of the label 30A which is on the most front side (on the side which is closest to the monitoring camera 20) in the depth direction of the image is generated. To that end, the marker 32B is extracted which is the closest to the marker 32A of the label 30A which is closest to the left end of the server rack 10A.

Such process is started with the label 30A which is closest to the left end of the server rack 10A, and continues by sequentially changing the group of the marker 32A and 32B to be generated to the right side one after another, so that the eight markers 32A and the eight markers 32B are divided into eight groups.

Then, the center of the marker 32A and the center of the marker 32B in each of the eight groups are detected, so that the scanning line connecting between the center of the marker 32A and the center of the marker 32B is set in each of the eight groups.

Further, in the case where the label 30A is searched for which is disposed next to a certain label 30A, the data indicating the distance ($\Delta X$ mm) between the labels 30A in the image on which the warping process has been performed may be used.

When the scanning lines are set, the level detector 52 scans the image of the indicators 31A along the scanning line in the lower-to-upper direction. In this case, the level detector 52 scans the pixels one by one of the indicators 31A disposed on the scanning line, and obtains the RGB signal levels of each of the pixels.

Further, based on the signal levels obtained by scanning the image of the indicators 31A on the eight scanning lines, the level detector 52 detects the temperatures indicated by the indicators 31A of the eight labels 30A as described below.

For each of the scanning lines, based on the signal levels obtained by scanning the image of the indicators 31A along the scanning line, the level detector 52 extracts eight signal levels corresponding to the positions of the eight indicators 31A. The data indicating the positions of the eight indicators 31A and the data indicating the positions of the markers 32A and 32B are stored in the memory 53.

Due to this, based on the positions of the markers 32A and 32B which are disposed on the respective ends of the scanning line and the positions of the positions of the eight indicators 31A (disposed between the markers 32A and 32B), it becomes possible to extract the eight signal levels corresponding to the positions of the eight indicators 31A.

By performing the process on the eight scanning lines, the temperatures indicated by the eight labels 30A can be obtained.

Further, for such a process which recognizes the image of the labels 30A, the matching is not performed on a fine pattern having a larger size. Actually, the pattern matching is performed on a fine pattern having a small size. Therefore, the lens aberration of the monitoring camera 20 does not cause a problem in the process.

FIG. 12 illustrates an example distribution of the temperatures indicated by the eight labels 30A.

Figures 12A, 12B:
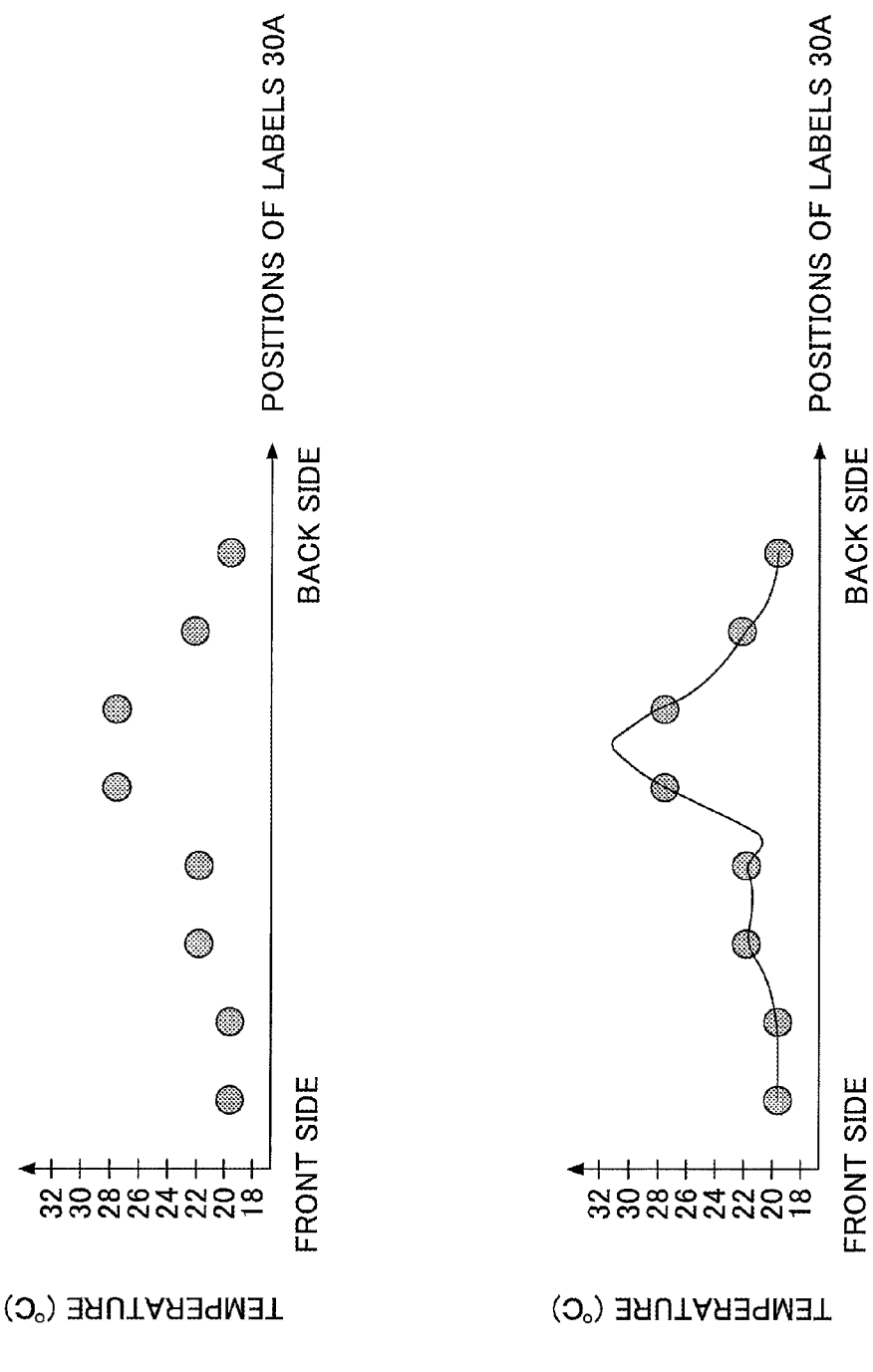
FIG. 12A illustrates example distribution of the temperatures indicated by eight labels 30A.
FIG. 12B illustrates the example distribution of the temperatures indicated by eight labels 30A.

In FIG. 12A, from the front side in the depth direction of the image (i.e., from the closest side of the monitoring camera 20), the temperatures indicated by the third and fourth labels 30A are slightly increased when compared with the temperatures indicated by the first and send labels 30A. Further, the temperatures indicated by the fifth and sixth labels 30A from the front side are further increased, and the temperatures indicated by the seventh and eighth labels 30A are decreased. As described, the temperatures indicated by the eight labels 30A can be obtained.

FIG. 12B illustrates a characteristic in which a curved line is fit which is obtained by performing an interpolation process on the distribution of the temperatures indicated by the eight labels 30A of FIG. 12A. For example, such curved line can be derived based on the consideration of the temperature distribution of air inside the data center 1 by three-dimensionally analyzing the data of the blowing port, exhaust port, and blowing air amount of the air-conditioning equipment in the data center 1 (see FIG. 3).

Next, with reference to FIG. 13, details of the warping process based on the perspective projection transformation are described.

FIG. 13 illustrates a principle of the warping process based on the perspective projection transformation. For explanatory purposes, with reference to FIG. 13, the warping process is described in a case where six labels 30A are mounted on the respective six server racks 10A.

As illustrated in FIG. 13A, it is assumed that the region 60AU is obtained with respect to the six labels 30A.

With respect to such region 60AU, the image transformation using the perspective projection transformation is performed. In the image on which the image transformation using the perspective projection transformation has not been performed (original image), the positions of the six labels 30A in the depth direction of the image are not arranged in place (differently arranged).

In contract, in the image on which the image transformation using the perspective projection transformation has been performed, as illustrated in FIG. 13B, the positions of the six labels 30A in the depth direction of the image are arranged in place (equally arranged). Specifically, by performing the transformation in a manner such that the number of pixels corresponding to the distance between the marker 32A and the marker 32B in the label 30A becomes the same number as much as possible among the six labels 30A of FIG. 13A, it becomes possible to obtain the positions of the labels 30A arranged in place (equally arranged) in the depth direction as illustrated in FIG. 13B. In FIG. 13B, the region 60AU is depicted with solid lines.

As illustrated in FIG. 13B, the region 60AU where the positions in the depth direction are differently arranged are transformed into the region 60AU1 where the positions in the depth direction are equally arranged. This transformation is achieved as a result of performing the transformation in a manner such that the number of pixels corresponding to the distance between adjacent markers 32A in the six labels 30A of FIG. 13A is equal to the number of pixels corresponding to the distance between adjacent markers 32B in the six labels 30A of FIG. 13A as much as possible. In this example, the labels 30A are mounted on the same position of the same server racks 10A. That is, the distances between the adjacent labels 30A in the six labels 30A are the same as each other. Therefore, the transformation is performed in a manner such that the number of pixels corresponding to the distance between the markers 32A is equal to the number of pixels corresponding to the distance between the markers 32B as much as possible. In a case, however, where the distances between the adjacent labels 30A are not constant, the transmission may be performed in a manner such that the ratio among the distances between the markers 32A and the ratio among the distances between the markers 32B in the actual space are equal to the ratio among the number of pixels corresponding to the distances between the markers 32A and the ratio among the number of pixels corresponding to the distances between the markers 32B, respectively, in the image on which the transformation has been performed. Such warping process based on the perspective projection transformation is performed on the images.

FIG. 14 illustrates an example method of determining the positions of the markers 32A and 32B when any of the markers 32A or 32B cannot be successfully read. In FIG. 14, the lateral (horizontal) direction and the vertical direction in the image on which the warping process has been performed are set as X axis and Z axis, respectively.

Further, the labels 30A in FIG. 14 have a parallelogram shape in which the right side is lower than the left side. This is due to the rotational transfer performed in the warping process.

Further, for explanatory purposes, with reference to FIG. 14, a method of setting the scanning line is described in a state where the six labels 30A are mounted on the six server racks 10A.

Further, the six markers 32A on the upper side are distinguished one from another by using the reference numerals 32A1, 32A2, 32A3, 32A4, 32A5, and 32A6 from the most front side in the depth direction as illustrated in FIG. 14. In the same manner, the six markers 32B on the upper side are distinguished one from another by using the reference numerals 32B1, 32B2, 32B3, 32B4, 32B5, and 32B6 from the most front side in the depth direction.

Figure 14A:
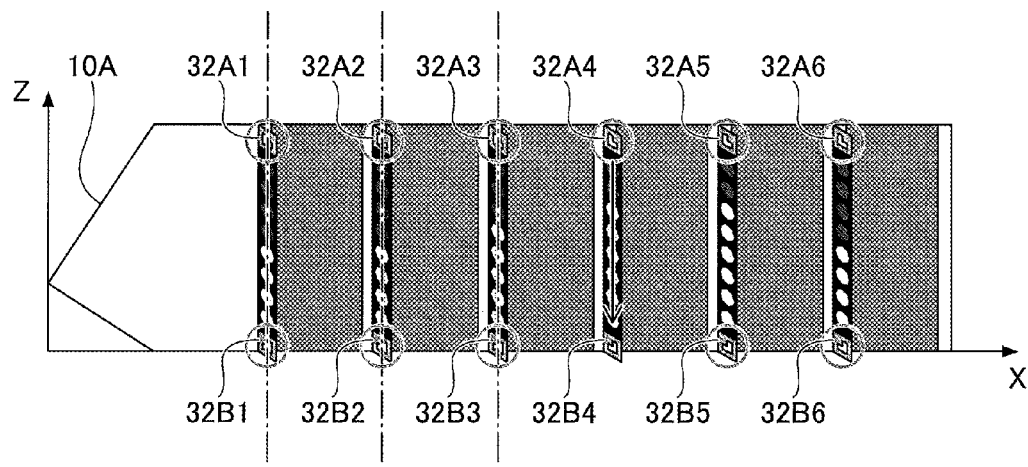
FIG. 14A illustrates an example method of determining the position of the marker 32A or 32B when the marker 32A or 32B, respectively, cannot be read.

More specifically, in FIG. 14A, for example, a case is described where the marker 32B4 cannot be read in the pattern matching.

In such a case, a straight line is set which is parallel to each of the straight lines which pass through the markers 32A1 and 32B1, the markers 32A2 and 32B2, and the markers 32A3 and 32B3, respectively, and which passes through the marker 32A4.

Further, the average Z coordinate value of the markers 32B1, 32B2, and 32B3 is calculated, so that the calculated average Z coordinate value is set to the Z coordinate value of the marker 32B4 on the straight line which passes through the marker 32A4. By doing this, the position of the marker 32B4 can be determined.

On the other hand, when the marker 32A4 cannot be read by the pattern matching, a straight line is set which is parallel to each of the straight lines which pass through the markers 32A1 and 32B1, the markers 32A2 and 32B2, and the markers 32A3 and 32B3, respectively, and which passes through the marker 32B4. Further, the average Z coordinate value of the markers 32A1, 32A2, and 32A3 is calculated, so that the calculated average Z coordinate value is set to the Z coordinate value of the marker 32A4 on the straight line which passes through the marker 32A4. By doing this, the position of the marker 32A4 can be determined.

Figure 14B:
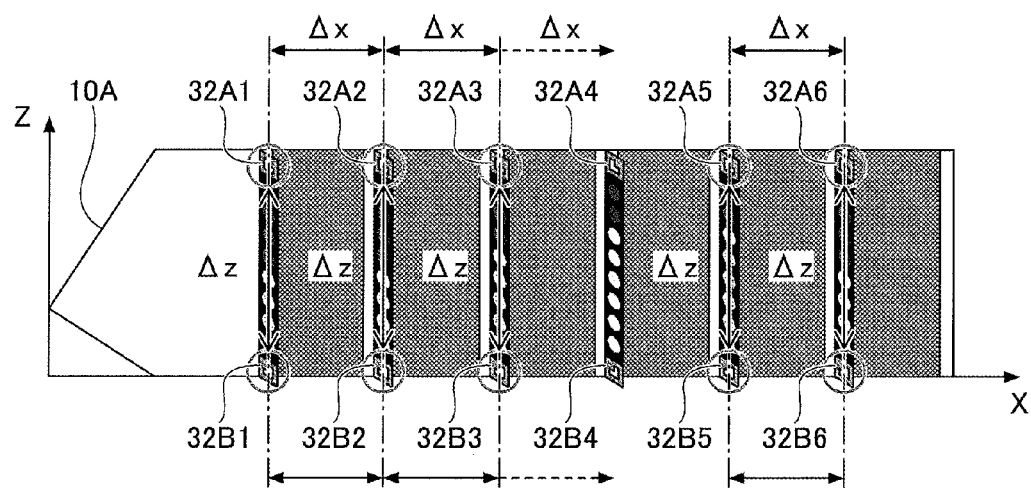
FIG. 14B illustrates the example method of determining the position of the marker 32A or 32B when the marker 32A or 32B, respectively, cannot be read.

FIG. 14B illustrates another example method in place of the method of FIG. 14A.

With reference to FIG. 14B, for example, a case is described where the markers 32A4 and 32B4 cannot be read in the pattern matching.

In such a case, an average value "$\Delta Z$" is calculated among the distance between the markers 32A1 and 32B1 in the Z axis direction, the distance between the markers 32A2 and 32B2 in the Z axis direction, the distance between the markers 32A3 and 32B3 in the Z axis direction, and the distance between the markers 32A51 and 32B5 in the Z axis direction.

Then, based on the average value "$\Delta Z$" and the distance "$\Delta X$ (mm)" which is between the labels 30A in the image on which the warping process has been performed, the positions of the markers 32A4 and 32B4 may be determined.

Further, in place of using the distance "$\Delta X$ (mm)" which is between the labels 30A in the image on which the warping process has been performed, the following method may be used.

An average value "$\Delta X$" is calculated among the distance between the markers 32A1 and 32A2 in the X axis direction, the distance between the markers 32A2 and 32A3 in the X axis direction, the distance between the markers 32A5 and 32B6 in the X axis direction. Then, based on the calculated average value "$\Delta X$" and the above average value "$\Delta Z$", the positions of the markers 32A4 and 32B4 may be determined.

By doing this, even when the markers 32A4 and 32B4 cannot be read, it becomes possible to determine the positions of the markers 32A4 and 32B4.

FIG. 15 illustrates a method of detecting the left end of the server rack 10A. Similar to FIG. 14, in FIG. 15, the lateral (horizontal) direction and the vertical direction in the image on which the warping process has been performed are set as X axis and Z axis, respectively.

Further, the labels 30A in FIG. 15 have a parallelogram shape in which the right side is lower than the left side. This is due to the rotational transfer performed in the warping process.

Further, the upper six markers 32A1, 32A2, 32A3, 32A4, 32A5, and 32A6 and the lower six markers 32B1, 32B2, 32B3, 32B4, 32B5, and 32B6 are described.

When the markers 32A1, 32A2, 32A3, 32A4, 32A5, and 32A6 are detected, by using the distance "ΔX (mm)" between the labels 30A, a rectangular region for testing is formed on each of the left and the right side of each of the markers 32A1 through 32A6 at the position separated from each of the markers 32A1 through 32A6 by "ΔX (mm)".

Similarly, when the markers 32B1, 32B2, 32B3, 32B4, 32B5, and 32B6 are detected, by using the distance "ΔX (mm)" between the labels 30A, a rectangular region for testing is formed on each of the left and the right side of each of the markers 32B1 through 32B6 at the position separated from each of the markers 32A1 through 32A6 by "ΔX (mm)".

Further, in place of using the distance "ΔX (mm)" between the labels 30A, the above average value "ΔX" may be used.

Figure 15A:
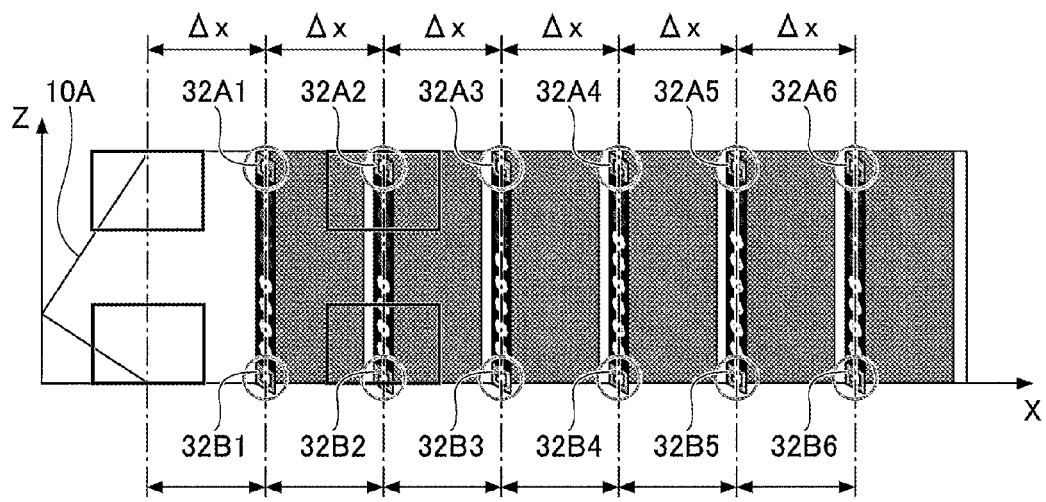
FIG. 15A illustrates an example method of detecting the left end of a server rack 10A.

FIG. 15A illustrates a state where the two rectangular regions are formed on both sides of the marker 32A1, and similarly, two rectangular regions are formed on both sides of the marker 32B1, so that four rectangular regions are formed.

Figure 15B:
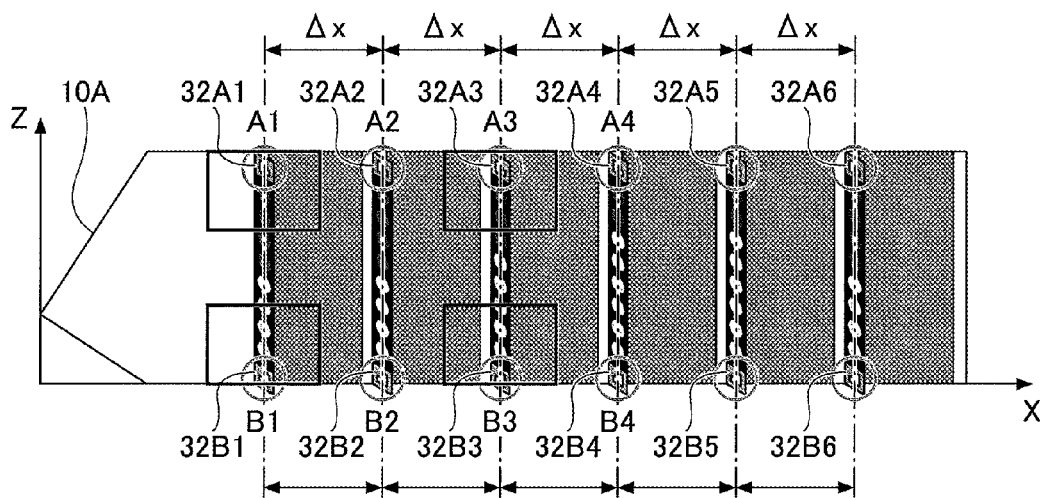
FIG. 15B illustrates the example method of detecting the left end of the server rack 10A.

Similarly, FIG. 15B illustrates a state where the two rectangular regions are formed on both sides of the marker 32A2, and similarly, two rectangular regions are formed on both sides of the marker 32B2, so that four rectangular regions are formed.

Further, for each of the images inside the rectangular regions, it is determined whether each of the image corresponds to an image of a corner part of the server rack 10A. In order to detect the left end of the server tack 10A, for example, an image indicating the corner part on the left side of each of the markers 32A1 and 32B1 is stored in the memory 53, and the pattern matching is performed.

Further, in a case where an image indicating the corner part is included in the rectangular region, the image includes not only the server rack 10A but also the inner walls 1B, the ceiling 1C, etc. Therefore, whether the corner part is included in the image may be determined based on signal levels of RGB color signals obtained from the image.

By detecting the corner part of the server rack 10A, it becomes possible to identify the label 30A which is the closest to the corner part of the server rack 10A. The label 30A closest to the corner part corresponds to the label 30A which is located at the position on the most front side (on the side closest to the monitoring camera 20) in the depth direction of the image.

Next, with reference to FIGS. 16 and 17, the temperature detection by using the label 30B and the humidity detection by using the label 30C are described.

Figures 16A, 16B:
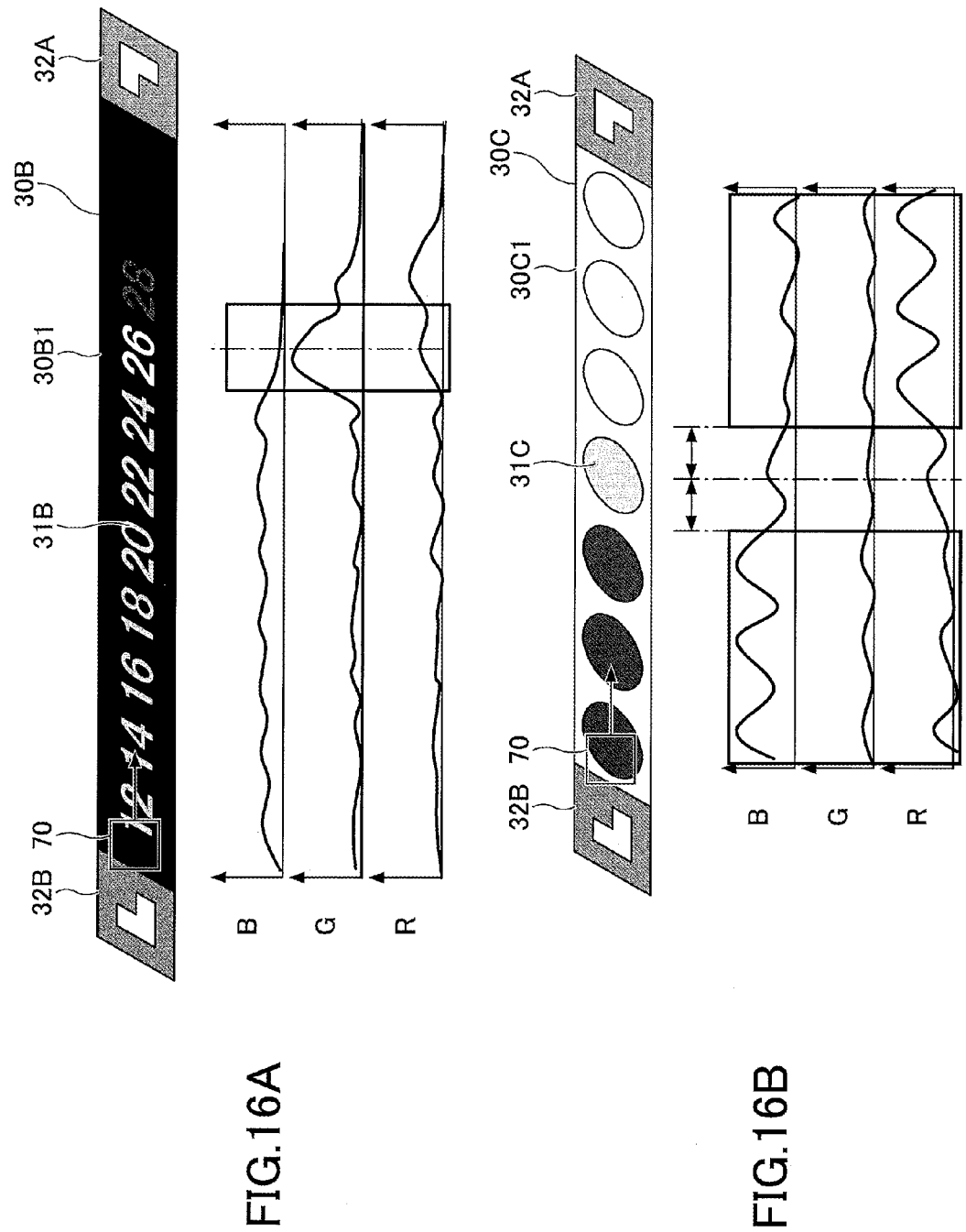
FIG. 16A illustrates temperature detection by the label 30B.
FIG. 16B illustrates humidity detection by the label 30C.

FIG. 16 illustrates an example of the temperature detection by using the label 30B and the humidity detection by using the label 30C. Here, the label 30B of FIG. 16A and the label 30C of FIG. 16B are the same as the label 30B of FIG. 2B and the label 30C of FIG. 2C, respectively. Note that, however, the labels 30B and 30C in FIG. 16 have been rotationally transferred in the warping process, so that each of the labels 30B and 30C has a parallelogram shape in which the right side is lower than the left side.

As described with reference to FIGS. 11B and 11C, when the temperature indicated by the label 30A is detected, the image of the indicators 31A is scanned pixel by pixel along the scanning line connecting between the center of the label 32A and the center of the label 32B, and the RGB signal levels at each of the pixels are obtained.

To that end, when the temperature indicated by the label 30B of FIG. 16A is detected a search window 70 which is for scanning the image on the scanning line pixel by pixel is used so that the RGB signal levels at each of the pixels are obtained.

When a ratio between the RGB signal levels corresponds to a predetermined ratio (range), it is determined that the image is within the display region of the indicators 31B. Further, a luminance distribution is weighted to the center of the display region. By doing this, when green color change (development) is detected, it becomes possible to detect the color change of the indicator 31B at the temperature of 26° C., of the label 30B.

On the other hand, when the humidity is detected by using the label 30C of FIG. 16B, the search window 70 which is for scanning the image on the scanning line pixel by pixel is used so that the RGB signal levels at each of the pixels are obtained.

In this case, when the environmental humidity exceeds the humidity allocated to each of the indicator 31C of the label 30C, the indictor 31C comes out in a blue color. On the other hand, when the environmental humidity is lower than the humidity allocated to each of the indicator 31C of the label 30C, the indictor 31C comes out in a pink color. Further, when the environmental humidity corresponds to the humidity allocated to each of the indicator 31C of the label 30C, the indictor 31C comes out in an intermediate color between blue and pink.

For example, by measuring the RGB color levels in the cases where the color read through the search window 70 is blue and pink and storing the measured RGB color levels when the color is blue and pink in the memory 53, it becomes possible to identify the indictor 31C which comes out in an intermediate color between blue and pink.

By doing this, for example, in the case of the RGB signal levels as illustrated in FIG. 16B, it is recognized that the color of the fourth indicator 31C counted from the marker 32B is the intermediate color. Therefore, it becomes possible to detect the color generation of the indicator 31C indicating "40%" of the label 30C.

FIG. 17 illustrates another example of the temperature detection by using the label 30B and the humidity detection by using the label 30C. The method of detecting the temperature and humidity illustrated in FIG. 17 is used when the image processing is performed in a gray-scale mode. Other than using the gray-scale mode, the method of FIG. 17 is the same as that of FIG. 16.

This method may be applied when, for example, the room of the data center 1 is dark, the infrared Light Emitted Diode (LED) of the monitoring camera 20 is used to irradiate the labels 30B and 30C, so that the image processing in the gray-scale mode is performed.

Figure 17A:
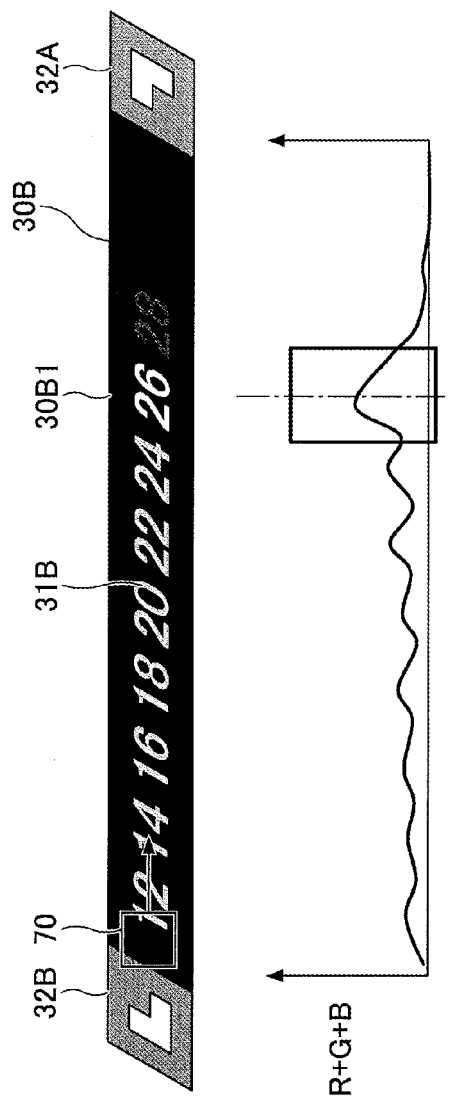
FIG. 17A illustrates temperature detection by the label 30B.

Specifically, in order to detect the temperature indicated by the label 30B of FIG. 17A, the search window 70 which is for scanning the image on the scanning line pixel by pixel is used so that the signal level indicating the sum of the RGB signal levels at each of the pixels is obtained.

When there exists one or more pixels whose signal level indicating the sum of the RGB signal levels is higher than that of the near-by pixels, the position of the pixel having the highest luminance from among the one or more pixels is determined as the position of the indicator 31B which corresponds to the environmental temperature. By doing this, it becomes possible to detect the color generation of the indicator which indicates "26° C." of the label 30B.

In this case, the indicator 31B which corresponds to the environmental temperature comes out green, and the indicator 31B which does not corresponds to the environmental temperature comes out in pale blue (generate weak blue light). Due to this, the indicator 31B, which corresponds to the environmental temperature and comes out green, has higher luminance.

Therefore, it is possible to detect the environmental temperature based on the luminance indicated by the signal level indicating the sum of the RGB signal levels.

Further, the humidity by using the label 30C of FIG. 17B can be detected by, for example, detecting as described below.

The indicators 31C of the label 30C come out in blue when the environmental humidity exceeds the respective humidities which are allocated to the indicators 31C. On the other hand, indicators 31C of the label 30C come out in pink when the environmental humidity is lower than the respective humidities allocated to the indicators 31C. Further, the indicators 31C of the label 30C, which corresponds to the environmental humidity, come out in an intermediate color between blue and pink.

The luminance values of the generated blue color, pink color, and the intermediate color between blue and pink differ from each other. Due to the differences, by measuring the luminance values of the generated blue color, pink color, and the intermediate color between blue and pink in advance, it becomes possible to detect the humidity by detecting the points whose luminance value is similar to that of the generated intermediate color.

Figure 17B:
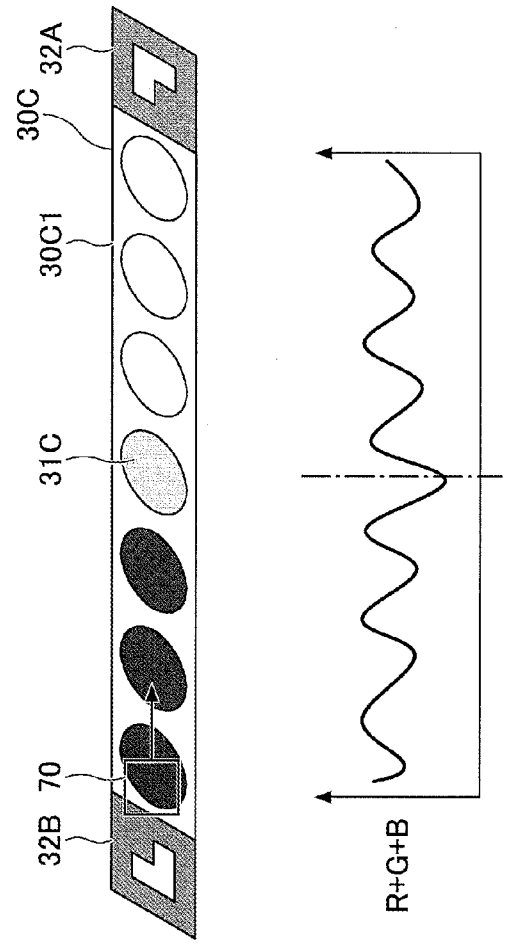
FIG. 17B illustrates humidity detection by the label 30C.

For example, in a case where the luminance value when the intermediate color is generated (comes out) is the lowest, as illustrated in FIG. 17B, it is recognized that the fourth indicator 31C counted from the marker 32B has the intermediate color. By doing this, it becomes possible to detect the generated color of the indicator indicating "40%" of the label 30C.

As described above, in the management system 100 according to an embodiment, it becomes possible to discretely (separately) measure the temperatures at a plurality of measurement points by mounting the labels 30A or 30B on the server racks 10A and 10B and performing the image processing on the images obtained by the monitoring camera 20.

Further, in the management system 100 according to an embodiment, it becomes possible to discretely (separately) measure the humidity at a plurality of measurement points by mounting the labels 30C on the server racks 10A and 10B and performing the image processing on the images obtained by the monitoring camera 20.

In related art, in the case where images are obtained (captured) by using the monitoring camera 20 whose number of pixels is not very large, in the image of the temperature and humidity labels which are arranged in the depth direction, there are no features in the display positions and the arrangement of the labels. Due to this, an error may be increased in identifying the pixels corresponding to temperature information, etc., disposed on the back (farther) side in the depth direction, so that it becomes difficult to obtain accurate temperature information, etc., of the labels especially arranged on the back side.

In contrast, in the management system 100 according to an embodiment, it becomes possible to discretely (separately) measure the humidity, etc., at a plurality of measurement points by mounting the labels 30A, 30B, and 30C which have specific features in their display positions and the arrangement as described above on the server racks 10A and 10B and performing the image processing on the images obtained by the monitoring camera 20.

In a case where the data center 1 includes the monitoring camera 20 and the computer system as illustrated in FIG. 5, it is very easy to install the management system 100 in the data center 1. That is, by mounting the labels 30A, 30B, or 30C on the server racks 10A and 10B and installing a program to cause the computer system 500 to function as the control apparatus 50, it becomes possible to install the management system 100 in the data center 1 as illustrated in FIG. 3.

In recent years, there have been many cases of the monitoring camera 20 being installed in such as the data center 1, so that the computer system 500 monitors the images obtained by the monitoring camera 20. In such a case, it becomes possible to install the management system 100 at very low cost.

Further, in a case where the data center 1 is newly constructed, if the monitoring camera 20 is to be installed, it becomes possible to add to the management system 100 with limited additional cost.

Further, note that installing the control apparatus 50 is not always necessary in the data center 1. That is, the control apparatus 50 may remotely detect the temperature or humidity from a site separated from the data center 1. For example, when the data center 1 is located in a remote location such as an isolated island, the control apparatus 50 may be disposed in an urban area.

Such management system 100 can be installed with limited cost because the number of the additional equipment sets necessary to be installed is limited and the installation work can also be minimized.

In the above description, with reference to FIG. 4, the difference in the imaging range is described between when the focal length is 2.8 mm and when the focal length is 3.6 mm. For example, when the resolution of the farthest label 30A is insufficient with the focal length of 2.8 mm alone, the image data may be obtained by integrating the images which are obtained with the focal lengths of 2.8 mm and 3.6 mm, so that the temperature or humidity can be detected based on the obtained integrated image data. For example, when the labels 30A are used, the following method may be used.

As an example integration method, first, the number of indicators 31A which are excluded (cut off) due to zoom magnification is stored as an initial value. When the focal length is 3.6 mm, the indicators 31 in the front side are offset in accordance with the initial value. Then, the image with the focal length of 3.6 mm is compared with the image with the focal length of 2.8 mm, so that the temperature data obtained by those images are integrated. Further, the image with the focal length of 3.6 mm and the image with the focal length of 2.8 mm can be obtained substantially at the same time. Therefore, the temperature data obtained from the two images may be integrated by treating the indicators 31A at the farthest positions in the two images as the same indicator 31A.

Figure 18:
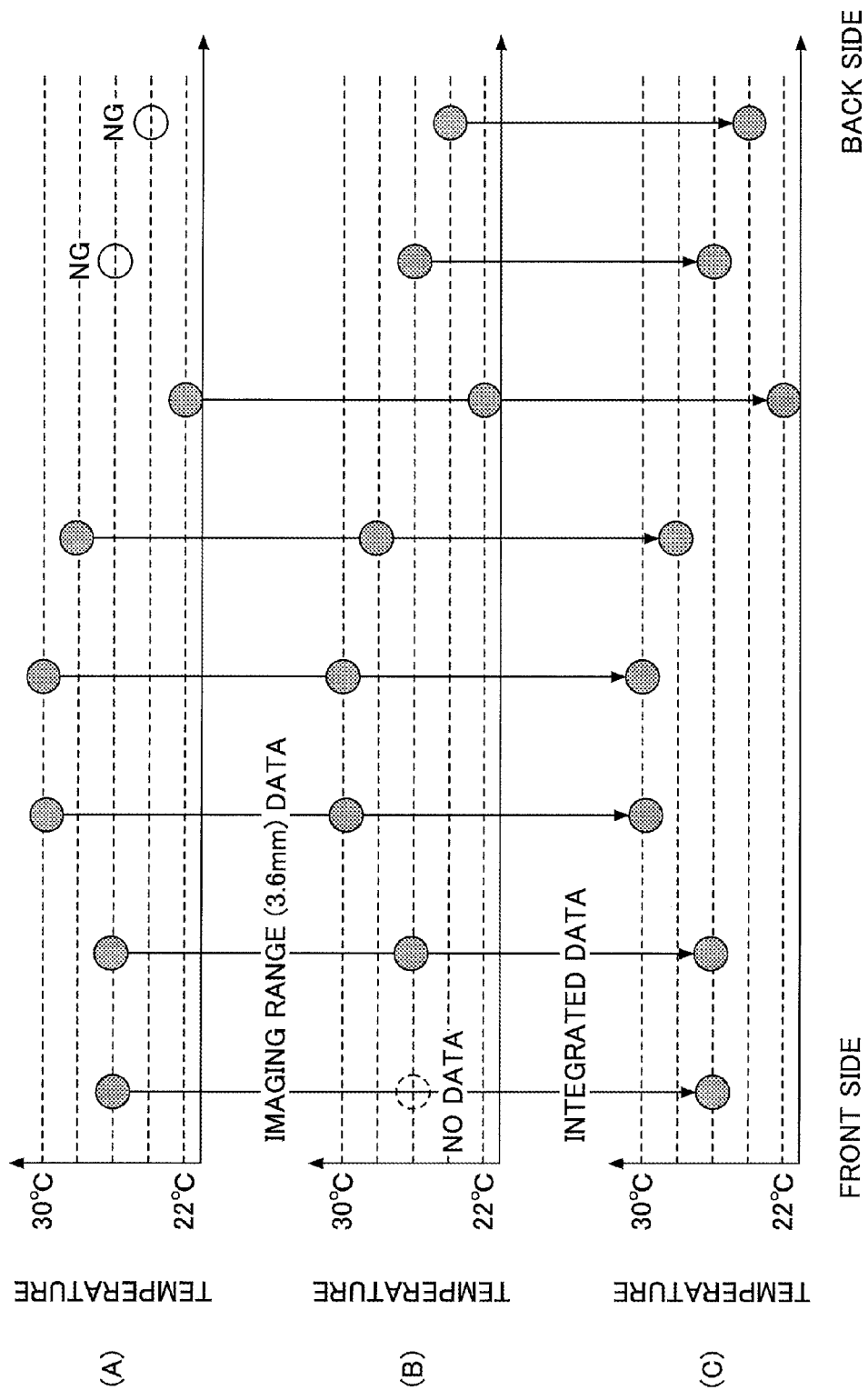
FIG. 18 illustrates an example integration method.

FIG. 18 illustrates an example of the integration method. More specifically, FIG. 18 illustrates an example result where the temperatures of the eight labels 30A are obtained based on the captured image data with the focal length of 2.8 mm and 3.6 mm.

In FIGS. 18A through 18C, in the lateral (horizontal) direction, the most front side (the side closest to the monitoring camera 20) in the depth direction in the images is on the left side, and the back side in the depth direction in the images (the side farthest from the monitoring camera 20) is on the right side. Part (A) of FIG. 18 illustrates the temperature distribution obtained when the image is captured with the focal length of 2.8 mm. Part (B) of FIG. 18 illustrates the temperature distribution obtained when the image is captured with the focal length of 3.6 mm. Part (C)

of FIG. 18 illustrates the temperature distribution obtained by integrating the temperature distribution with the focal length of 2.8 mm and the temperature distribution with the focal length of 3.6 mm.

Here, as illustrated in part (A) of FIG. 18, it is assumed that the temperatures of the two labels 30A on the back side cannot be detected by performing the image processing on the image captured with the focal length of 2.8 mm. Also, as illustrated in part (B) of FIG. 18, it is assumed that the temperature of the label 30A on the most front side cannot be detected by performing the image processing on the image captured with the focal length of 3.6 mm. Further, it is assumed that with respect to the rest of the labels 30A, the same results of the temperatures are obtained based on the image captured with the focal length of 2.8 mm and the image captured with the focal length of 3.6 mm.

In such a case, as illustrated in part (C) of FIG. 18, the temperature distribution obtained with the focal length of 2.8 mm and the temperature distribution obtained with the focal length of 3.6 mm may be integrated by employing (using) the temperature distribution obtained with the with the focal length of 2.8 mm as the detection temperature of the label 30A on the most front side and further employing (using) the temperature distribution obtained with the with the focal length of 3.6 mm as the detection temperatures of the two labels 30A on the back side.

Further, in the above description, a case is described where the labels 30A are mounted at the same height positions on the server racks 10A and 10B. Note that, however, the labels 30A may be mounted on the positions of different heights.

Figure 19A:
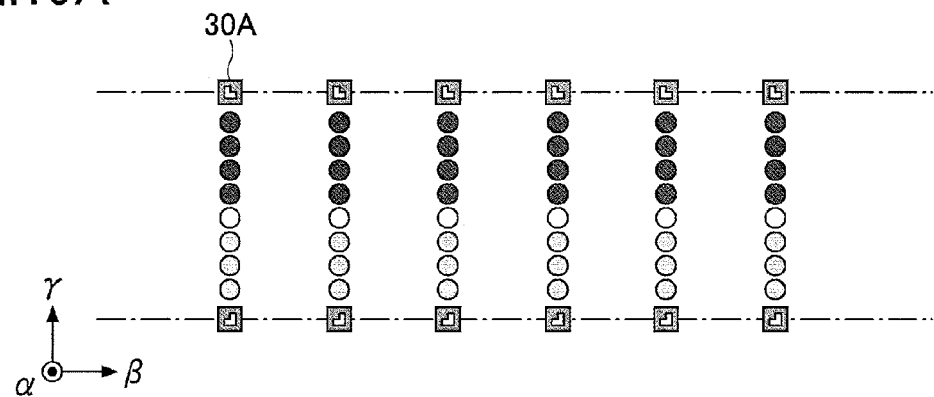
FIG. 19A illustrates a variation of positional relationships between the labels 30A.
Figure 19B:
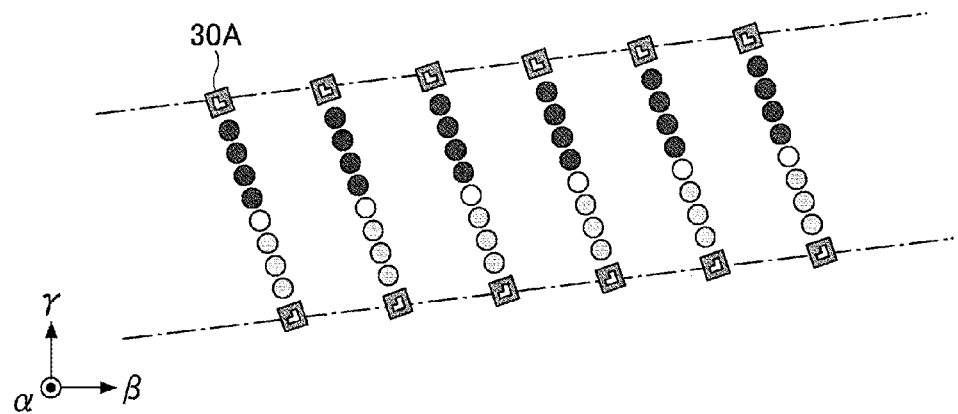
FIG. 19B illustrates a variation of positional relationships between the labels 30A.
Figure 19C:
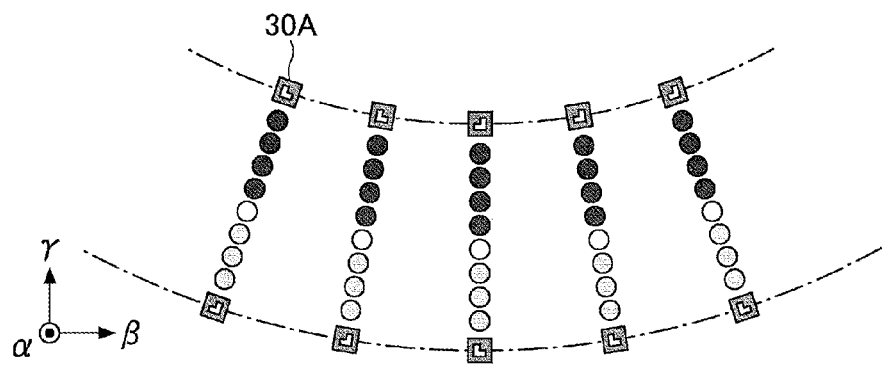
FIG. 19C illustrates a variation of positional relationships between the labels 30A.

FIG. 19 illustrates various positional relationships of the labels 30A. Each of FIGS. 19A through 19C schematically illustrates positional relationships between six labels 30A viewed from the pathway 1A side. FIG. 19 illustrates αβγ coordinate system similar to FIG. 3.

Among ten points included in each of the labels, the point at the upper end and the point at the lower end indicate the markers 32A and 32B, respectively. The remaining eight points indicate the eight indicators 31A. Among the eight indicators 31A, the point having a pale color indicates the environmental temperature.

In FIG. 19A, the six labels 30A are arranged at the same interval along the β axis and in parallel to the γ axis. This arrangement corresponds to that of the labels 30A of FIG. 3A. In a case of the arrangement of the six labels 30A of FIG. 19A, the indicators 31A, which are included in the labels 30A in the image captured in the β axis direction, are scanned in the γ axis direction. Due to this, it becomes possible to obtain luminance values of the indicators 31A. Note that if the image capturing direction (imaging direction) is equal to the arranging direction of the indicators 31A, scanning cannot be performed. Therefore, it is desired that the image capturing direction differs from the arranging direction of the indicators 31A.

For example, as illustrated in FIG. 19B, the arranging direction of the indicators 31A may be inclined relative to the arranging direction of the indicators 31A of FIG. 19A. Further, as illustrated in FIG. 19C, the indicators 31A may be arranged along an arc. In either case, the image capturing direction (the β axis direction) differs from the arranging direction of the indicators 31A. Therefore, it is possible to scan the indicators 31A to obtain the luminance values thereof.

Further, in the above description, a case is described where the memory 53 stores the data which indicate the positional relationship between the labels 30A in advance.

Note that, however, without using the data indicating the positional relationship between the labels 30A, it is still possible to read the detection temperatures of the labels 30A.

In this case, the image processing to recognize the image of a plurality of indicators 31A by using the size data which indicate the sizes of the labels 30A is done without performing the warping process. Such image processing is an example of the second image processing. That is, the second image processing is a process to recognize the image of the indicators 31A by using the information of the number of pixels corresponding to the labels 30A in the captured image data.

Figure 20A:
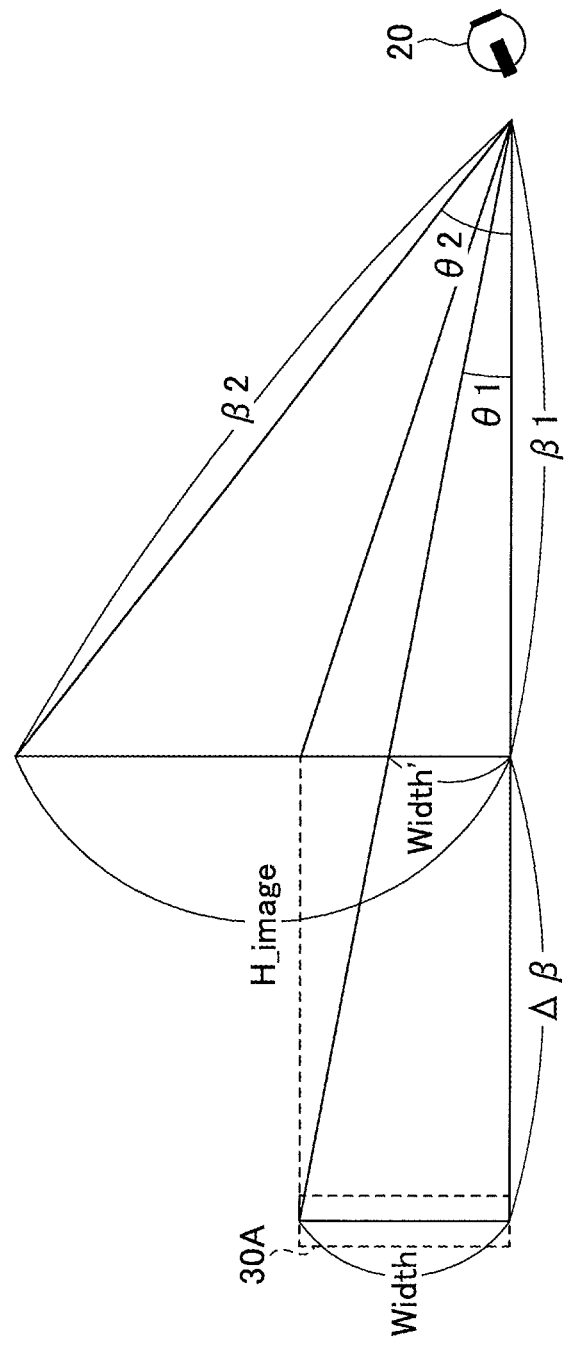
FIG. 20A illustrates an example method of deriving the interval between the labels 30A.

FIG. 20A illustrates an example of a method of deriving the distance between labels 30A.

FIG. 20A illustrates a range, which is captured by the monitoring camera 20 disposed on the right end, in a planar manner, to illustrate a method of so-called "paraxial calculation". It is assumed that the label 30A whose image is captured by the monitoring camera 20 is disposed on the left side of the monitoring camera 20 in the horizontal direction and the size of the label 30A in the longitudinal direction (vertical direction) is "Width". Here, the distance from the monitoring camera 20 to the label 30A is "β1+Δβ".

Further, the maximum image height of the image having the captured label 30A with the focal length of "F" is expressed as "H_image", the number of pixels in the horizontal direction and the vertical direction of the monitoring camera 20 are expressed as "N_H" and "N_V", respectively, the distance from the monitoring camera 20 to the image (where the maximum image height "H_image" is obtained) is expressed as "β", and the pixel size of the monitoring camera 20 is expressed as "d". Further, the distance from the monitoring camera 20 to the point where the maximum image height "H_image" is obtained is expressed as "β2".

Here, the angle formed by the size "Width" in the longitudinal direction of the label 30A relative to the monitoring camera 20 is expressed as "θ1", and the angle formed by the maximum image height "H_image" relative to the monitoring camera 20 is expressed as "θ2".

Actually, the size "Width" in the longitudinal direction of the label 30A and the maximum image height "H_image" are very small relative to the distance "β1+Δβ" from the monitoring camera 20 to the label 30A. Therefore, the actual angles "θ1" and "θ2" are very small.

Further, although the actual distance from the monitoring camera 20 to the label 30A is "β1+Δβ", as illustrated in FIG. 20A, in the image where the maximum image height "H_image" is obtained, the label 30A is imaged as if the label 30A were positioned at the distance "β1" from the monitoring camera 20.

Here, for simplifying purposes, in the monitoring camera 20, it is assumed that the pixel size in the horizontal direction is the same as that in the vertical direction.

In such a case, by paraxial approximation, the following Formula (8) is satisfied.

$$H\_image \div \beta = 0.5 \times d \times \sqrt{(N\_H)^2 + (N\_V)^2} \div F \quad \text{Formula (8)}$$

Here, the multiplication by "0.5" is included in the right side. This is because it is desired to reduce the number of pixels by half in consideration of the image height.

Here, the apparent width in the image of the indicator 31A which is imaged at the position "β1" is expressed as "Width'". Since actual width of the indicator 31A is "Width", the number of the pixels to be used is multiplied by "Width÷H_image".

On the other hand, in a case where the actually obtained number of pixels is multiplied by "A", since the difference between the position of the indicator 31A and the position of "β1" is "Δβ", the following Formulas (9) and (10) are satisfied. Here, the angles "θ1" and "θ2" are very small, therefore β1≈β2 is satisfied. Therefore, it is assumed that "β1" and "β2" is equal to "β".

$$Width \div (\beta + \Delta\beta) = Width' \div \beta \qquad \text{Formula (9)}$$

$$Width' = \beta \div (\beta + \Delta\beta) \times Width = A \times Width \qquad \text{Formula (10)}$$

Based on Formulas (9) and (10), the following Formula (11) can be derived.

$$A = \beta(\beta + \Delta\beta) \qquad \text{Formula (11)}$$

According to Formula (11), when the focal length "F", the maximum image height "H_image", the number of pixels "N_H" and "N_V", the apparent number of pixels of the indicator 31A (i.e., the number of pixels of the indicator 31A in the image), and the actual width of the indicator 31A "Width" are known, it becomes possible to identify the distance from the monitoring camera 20 to the indicator 31A at the position of β (β1).

FIG. 20B illustrates an example of the size data. For each of the focal lengths (zoom magnifications), the maximum occupancy number of pixels for each of the labels in horizontal and vertical directions of the image is stored as illustrated in FIG. 20B. Further, the image path and the file name are also stored, which are for the pattern matching used to search for the labels. Note that, however, the image path and the file name for the pattern matching may be generated by using the width and the length illustrated in FIG. 20B based on a reference image. According to the order of the label numbers, the pattern matching is performed on the image data. When there exists a pixel position where at least a predetermined degree of matching can be obtained (indicated), the pixel position is determined as the center position of the label. For example, as the degree of matching, the normalized cross-correlation coefficient is used. When the pattern matching is performed, the longitudinal direction in the image data of the label can be determined. Therefore, for example, when the center position is moved in the direction parallel to the longitudinal direction by a predetermined number of pixels, the center position reaches the end point of the label.

The number of pixels corresponding to the label closer to the monitoring camera 20 is relatively large. Therefore, good degree of matching can be obtained. On the other hand, the label which is further from the monitoring camera 20 may not be searched for and detected because it is difficult to obtain a good degree of matching. However, if the labels near the monitoring camera 20 can be detected based on such size data, by using the extrapolation view of the outer shape of the labels and the size data as illustrated in FIG. 20B, it becomes possible to identify the position of the label whose position could not be searched for and detected based on the degree of matching. FIG. 20C illustrates an example. FIG. 20C illustrates the same configuration as that of FIG. 13. However, there are no markers 32A and 32B. Here, a case is considered where only four labels closer to the monitoring camera 20 can be searched for. According to the size data of FIG. 20B, the number of labels that cannot be searched for and detected is two. By using the pattern matching results of the four labels, a center line which passes through the center points of the labels is obtained. Further, by using the center points of the labels, the orientation of the labels (i.e., the direction corresponding to the longitudinal direction of the labels), and the size data, it becomes possible to set two extrapolation lines of the labels.

When the position can be found where the distance between the two extrapolation lines corresponds to the length indicated in the size data, it is possible to estimate that the label exists at the position.

As described above, without using the data which indicate the positional relationship between the labels 30A, it is still possible to read the detection temperatures of the labels by performing the imaging processing to identify the image of the indicators 31A using the size data indicating the sizes of the labels 30A.

FIG. 21 illustrates the labels 30D, 30E, and 30F according to a modified example of the first embodiment.

Figures 21A, 21B:
FIG. 21A illustrates labels 30D according to one modified example of the first embodiment.
FIG. 21B illustrates labels 30E according to one modified example of the first embodiment.

The label 30D of FIG. 21A is the same as the label 30B except that the markers 32A and 32B are excluded from the label 30D (see FIG. 2B). That is, in the label 30D, eleven indicators 31D are formed on the sheet 30D1. The indicators 30D are the same as the indicators 31B.

When such label 30D is used, instead of recognizing the markers 32A and 32B by the pattern matching as described above, the entire rectangular shape of the label 30D is recognized (identified) by the pattern matching.

Figure 21C:
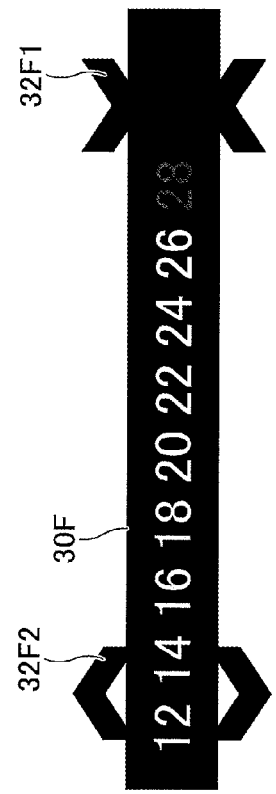
FIG. 21C illustrates labels 30F according to one modified example of the first embodiment.

Further, the labels may have a characteristic shape such as the shapes of the labels 30E and 30F of FIGS. 21B and 21C, respectively. The label 30E of FIG. 21B has a shape where the protruding sections 32E1 and 32E2 having a shape something like a tip of an arrow are added to the shape of the label 30D.

Further, the label 30F of FIG. 21C has a shape where the protruding sections 32F1 and 32F2 having a shape something like a tip of an arrow are added to the shape of the label 30D.

When such label 30E or 30F is used, the label 30E or 30F can be recognized by performing the pattern matching on the entire shape of the label 30E or 30F, respectively. Further, when the scanning line is set (determined), the scanning line is determined by connecting the center coordinates between the two protruding sections 32E1 and the center coordinates between the two protruding sections 32E2. This method can also be applied to the protruding sections 32F1 and the 32F2.

Further, there may be a case where a cable, etc., is wrongly detected. In view of this, preferably, for example, the pattern matching may be performed on the entire shape of the labels 30D, 30E, or 30F of FIGS. 21A, 21B, and 21C, respectively, and then, the markers 32A and 32B are detected. For example, it is determined that the label is detected when each degree of matching of the entire shape of the label 30D, 30E, or 30F and the labels 32A and 32B is 0.3 or more.

In this embodiment, the warping process is performed by assuming that the labels adjacent to each other are arranged along the camera optical axis. Note that, however, it is not always necessary that the labels adjacent to each other are arranged along the camera optical axis. This is because the warping can be performed in the image data as long as, for example, the relationship between the labels closer to the camera and the camera optical axis and the relationship between the labels farther from the camera and the camera optical axis in the image are expressed in a formula or an array in advance. Further, when the labels are arranged in alignment, it is not necessary that the labels are arranged along the camera optical axis and the distances between the labels and the camera optical axis are expressed in a formula or an array. This features is also applied to other embodiments and is common in the preset invention. Second embodiment The management system 100 (see FIG. 3A) according to a second embodiment is applied to a poultry house.

Figure 23:
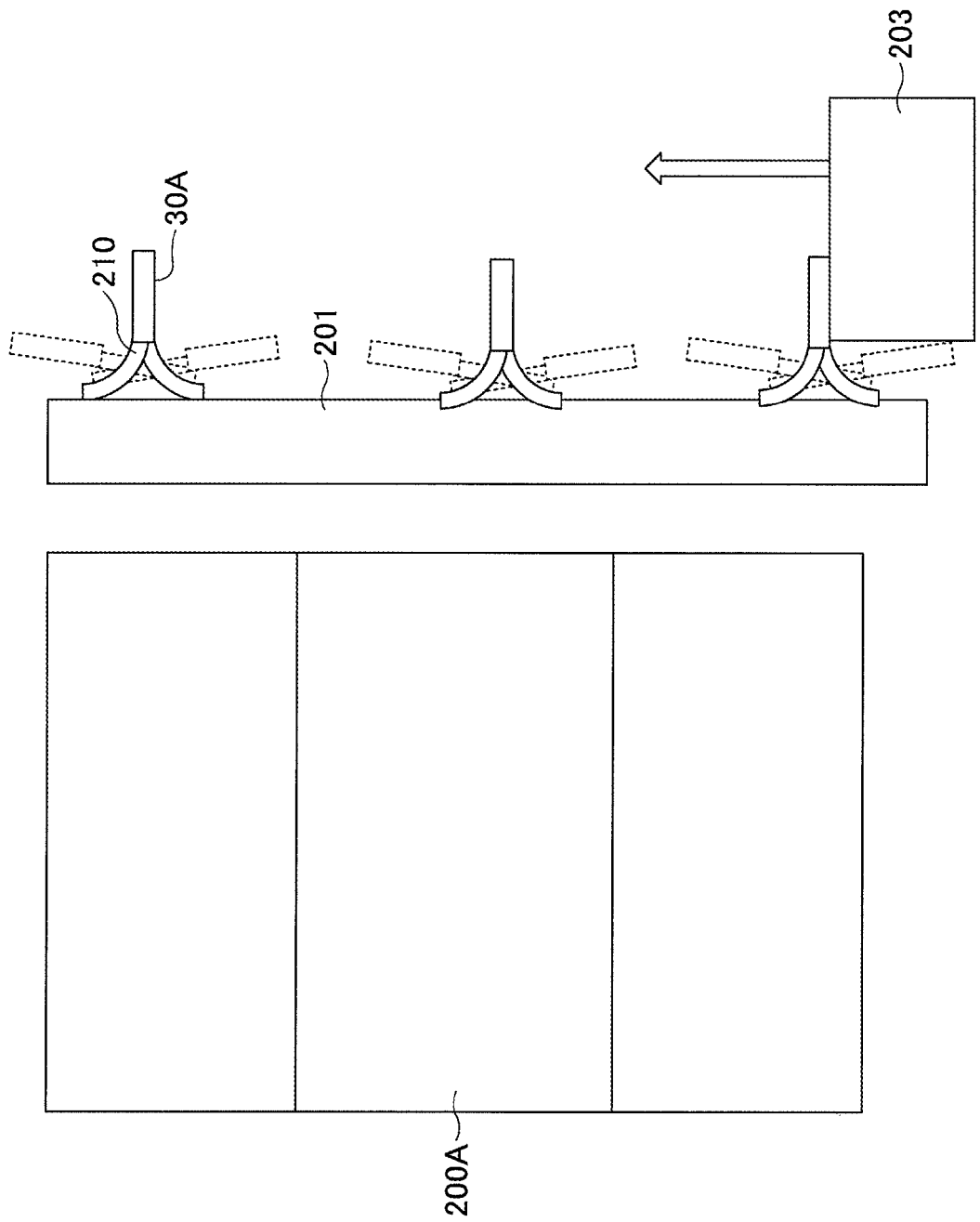
FIG. 23 illustrates an example plane composition of a part of FIG. 22.

FIG. 22 illustrates the inside of a poultry house. FIG. 23 illustrates a planar configuration of a part of FIG. 22.

As illustrated in FIG. 22, inside the poultry house, there are cages 200A and 200B for raising chickens. This configuration differs from that of FIG. 3 in that, for example, the server racks 10A and 10B of the data center 1 (in FIG. 3) are replaced by the cages 200A and 200B.

On each of the cages 200A and 200B, a feed gutter 201 and an egg collection gutter 202 are mounted. Food is distributed to the feed gutters 201 at set timings by an automatic feeder 203. Chickens eat food distributed to the feed gutter 201, and lay eggs. The eggs are automatically collected via the egg collection gutter 202.

In such a poultry house, it is important to manage temperature and humidity. To realize the temperature management and the humidity arrangement, the labels 30A and 30C (see FIGS. 2A and 2C) are mounted on the feed gutters 201 and the egg collection gutters 202, respectively and the image processing is performed on the images captured by the monitoring camera 20.

Further, as illustrated in FIG. 23, the labels 30A are mounted on the feed gutter 201 via a folding mechanism 210. By doing this, it becomes possible to prevent the labels 30A from blocking the passage of the automatic feeder 203. As the folding mechanism 210, by using a spring, etc., it is preferable to normally hold the label 30A at the position as illustrated in FIG. 22.

Further, in the poultry house, it is also desired to manage the viability status of the chickens. To detect the viability status of the chickens, for example, the image processor 51 may determine whether the luminance of each pixel of the part other than the part of the labels 30A and 30C in the image captured by the monitoring camera 20 changes in time series. This is because while the chickens are alive, the luminance of each pixel of the part other than the part of the labels 30A and 30C changes in time series.

Third Embodiment

In a third embodiment, the management system 100 (see FIG. 3A) is applied to a glass house.

Figure 24:
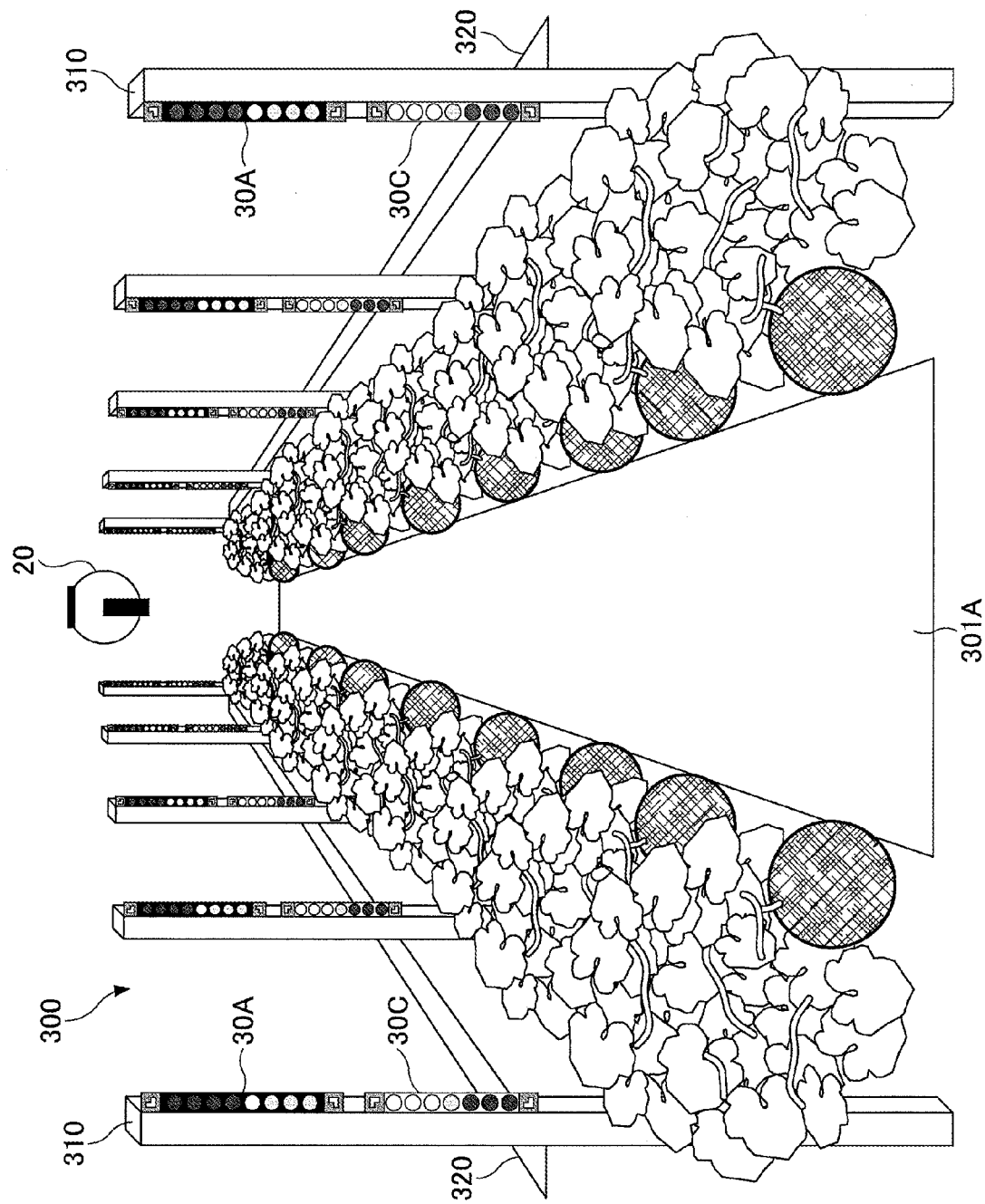
FIG. 24 illustrates an example inside of a glass house 300.

FIG. 24 illustrates an inside of a glass house 300.

Inside the glass house 300, crops are planted along a pathway 301A to grow fruit or vegetables. In such a glass house 300, it is important to manage temperature and humidity.

To realize the management of the temperature and the humidity, the labels 30A and 30C (see FIGS. 2A and 2C) are mounted on the poles 310 and the image processing is performed on the images captured by the monitoring camera 20.

Inside the glass house 300, water is supplied to the crops by using a watering path 320. Therefore, when the management system 100 (see FIG. 3A) can manage the temperature and the humidity, it becomes possible to greatly improve the efficiency of farm working.

Further, sunlight enters into the glass house 300, which may affect the reading of the labels 30A and 30C.

In greenhouse horticulture or a plant factory using the glass house 300, the accumulated luminance is in association with the time of bloom and the growing rate. The management system 100 according to the third embodiment can calculate the luminance as well. More detail is described with reference to FIG. 25.

Figure 25:
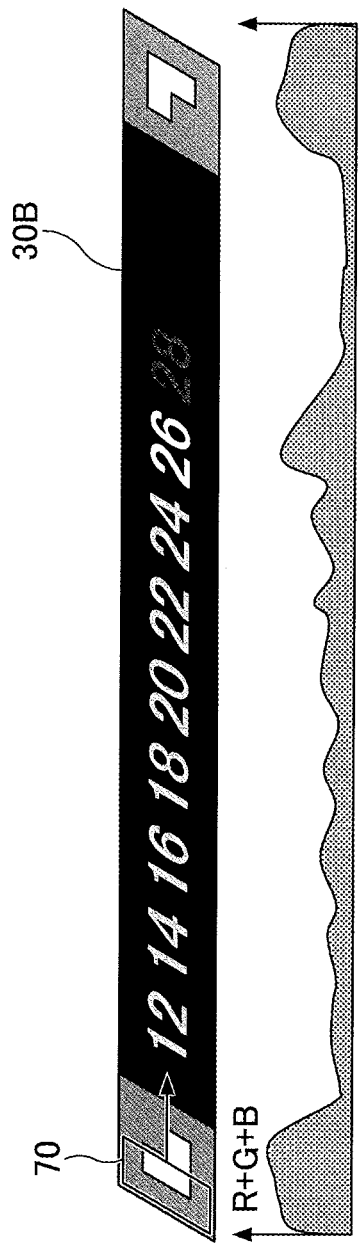
FIG. 25 illustrates an example method of calculating luminance by a management system 100 according to a third embodiment.
Figure 26:
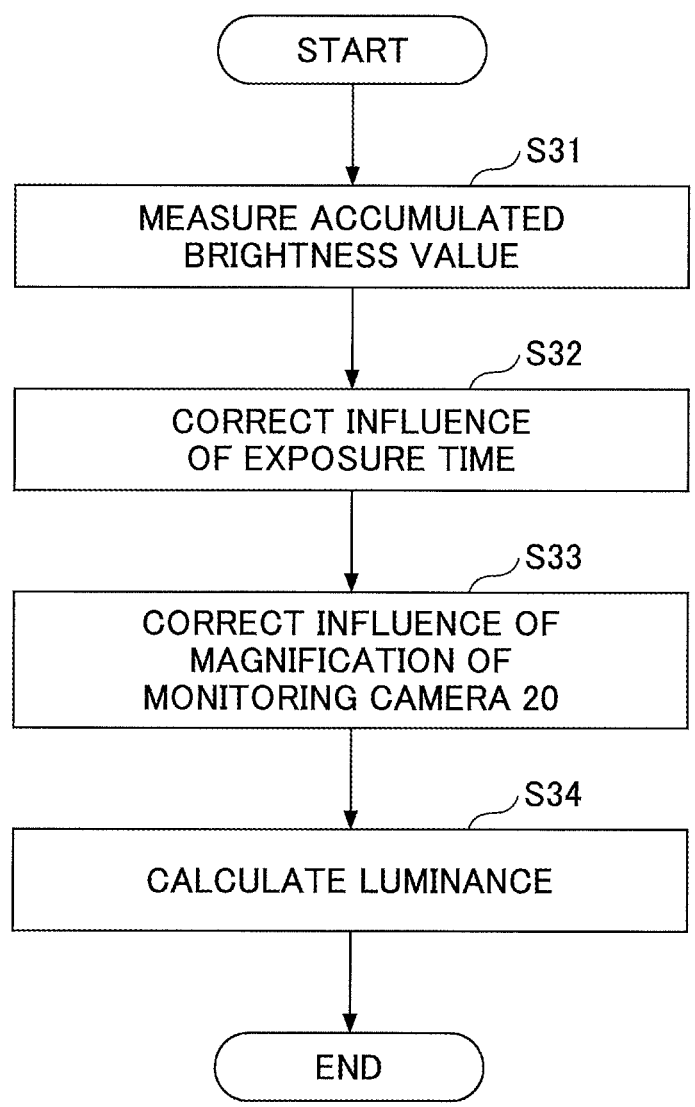
FIG. 26 is an example flowchart of a procedure of calculating the luminance by the management system 100 according to the third embodiment.

FIG. 25 illustrates an example method of calculating the luminance by the management system 100 according to the third embodiment. FIG. 26 is an example flowchart of the procedure to calculate the luminance by the management system 100 according to the third embodiment. The process of FIG. 26 is executed by the level detector 52.

First, as a precondition, the luminance is calculated by using a gray-scale image. When images are captured in the daytime, the images are captured by setting (adjusting) the irradiation time (exposure time) to the pixels in a manner such that the maximum RGB brightness in the image of the labels 30A and 30C is not saturated, and the color image data are converted into the gray-scale data. Further, in the calculation of the gray scale, a value may be used which is obtained by normalizing the sum of the RGB brightness values (R+G+B) by using the sum of the maximum RGB brightness values.

Under such precondition, the level detector 52 scans the labels 30A and 30C from a predetermined coordinates of the marker 32A to predetermined coordinates of the marker 32B by using the search window 70 to measure the accumulated brightness value in the search window 70 (step S31).

In step S31, the brightness, which is obtained from the image in the search window 70, is integrated to determine a preliminary luminance value in a first stage at that time. The integration of the brightness is performed by excluding the indicators 31A which do not indicate the environmental temperature (see FIG. 2A) and the indicators 31C (see FIG. 2C). For example, in the case of 30A, as illustrated in FIG. 25, when the environmental temperature is 26° C., the brightness of the indicators 31A other than the indicator 31A which generates color of "26° C." is not integrated. This is because those indicators do not indicate the environmental temperature and do not generate color as well.

The preliminary luminance value in the first stage is stored as first data in a table format in association with the accumulated brightness value relative to the exposure time.

Next, the level detector 52 corrects the influence by (of) the exposure time by eliminating the influence by the imaging of the monitoring camera 20 by using the first data (step S32). In the glass house 300 where sunlight enters, the intensity of sunlight varies depending on time zone, so that the brightness of the image varies. This is because the influence by the exposure time is corrected. When the influence by the exposure time is corrected which is included the preliminary luminance value in the first stage included in the first data, a preliminary luminance value in a second stage is obtained. The preliminary luminance value in the second stage is stored as second data in a table format in association with the accumulated brightness value relative to the exposure time.

For example, the relationship of the accumulated brightness values relative to the exposure time can be calculated by acquiring the values of the exposure time and the brightness value while changing the exposure time in a short time period when the management system 100 is initially operated. Further, the relationship of the accumulated brightness values relative to the exposure time may be calculated by performing measurement more than once while the exposure time is changed until the next measurement.

Next, the level detector 52 corrects the influence by the magnification of the monitoring camera 20 which is included in the preliminary luminance value in the second stage included in the second data (step S33).

When the magnification of the monitoring camera 20 changes, the number of pixels indicating the label 30A in the image changes. Further, the number of pixels of the label 30A closer to the monitoring camera 20 differs from the number of pixels of the label 30A farther from the monitoring camera 20 in one image. Due to this, even under the same luminance, it appears that the brightness value of the label 30A closer to the monitoring camera 20 is greater.

Therefore, when the management system 100 is installed, for each of the images of the labels 30A closer to the monitoring camera 20 and the labels 30A farther from the monitoring camera 20 having substantially the same luminance, the number of pixels in use and the accumulated brightness value are measured, so that the data are generated (prepared) indicating the relationship between the number of pixels in use and the accumulated brightness value of the labels 30A. When the data are prepared, for each of the images captured with various luminances, the brightness of the labels 30A closer to the monitoring camera 20 and the brightness of the labels 30A farther from the monitoring camera 20 are compared, so that normalized integrated brightness values are used so as to reduce the difference between the brightness values regardless of the luminance value. By doing this, the influence by the magnification is corrected.

In step S33, by correcting the influence by the magnification included in the preliminary luminance value in the second stage included in the second data, a preliminary luminance value in a third stage is obtained. The preliminary luminance value in the third stage is stored as third data in a table format in association with the relationship of the accumulated brightness value relative to the exposure time.

Next, the level detector 52 calculates a final luminance by comparing the preliminary luminance value in the third stage in the third data with the luminance value indicated by a commercially-available luminance meter (step S34). That is, the preliminary luminance value in the third stage is converted into the luminance value obtained by the luminance meter.

The luminance value of the label 30A varies depending on the luminance orientation. Due to this, in the conversion, in the case of artificial light such as light from lighting, a database of the orientation and the number of lights may be used and in the case of natural light, the database of the influences of time and season may be used.

As described above, by capturing the images of the labels 30A indicating the temperature and the label 30C indicating the humidity by using the monitoring camera 20, it becomes possible to measure the temperatures, humidities, and luminances in the sites (areas) of the glass house 300.

In the case where a difference between any of the temperature, humidity, and luminance and any of these current target values exceeds a predetermined value, it is desired to use the air-conditioner, lights, curtains, etc., to correct and set appropriate temperature, humidity, and luminance values.

In the management system 100 according to the third embodiment, it is possible to obtain the luminance in addition to the temperature and the humidity by image processing. In a facility where crops are produced such as the glass house 300, the luminance is a parameter which relates to the growth of the crops. Therefore, agriculture in a remote location becomes possible, and it becomes more convenient.

Further, in the glass house 300, it is desired to protect crops from being stolen. To that end, for example, the level detector 52 may determine whether the brightness of the pixels of the part other than the part of the labels 30A and 30C changes in time series in the images captured by the monitoring camera 20. By doing this, it becomes possible to detect whether there exists an illegal intruder in the glass house 300. This is because when there is an illegal intruder, the brightness of the pixels of the part other than the part of the labels 30A and 30C changes in time series.

All examples and conditional language recited herein are intended for pedagogical purposes to aid the reader in understanding the invention and the concepts contributed by the inventors to furthering the art, and are to be construed as being without limitation to such specifically recited examples and conditions, nor does the organization of such examples in the specification relate to a showing of superiority or inferiority of the invention. Although the embodiments of the present inventions have been described in detail, it is to be understood that various changes, substitutions, and alterations could be made hereto without departing from the spirit and scope of the invention.

What is claimed is:

1. A management system comprising:
a plurality of labels disposed on a management target at respective positions different from each other in a direction separating from an imaging device, each of the labels including a plurality of display parts, the plurality of display parts being configured to change respective colors depending on different levels of temperature or humidity with each other, the plurality of display parts being arranged so as to change coloring positions depending on level of temperature or humidity;
an imaging device configured to output image data indicating an image of the labels captured by the imaging device;
an image processor configured to perform first image processing or second image processing, the first image processing being configured to transform the image data in a manner such that a difference in a number of pixels corresponding to each of the labels among the labels in image data after the transformation is less than a difference in the number of pixels corresponding to each of the labels among the labels in the image data before the transformation, the second image processing being configured to recognize an image of the plurality of display parts by using information of the number of pixels corresponding to each of the labels in the image data; and
a level detector configured to detect the level of temperature or humidity based on brightness information of pixels corresponding to the display parts, the brightness information obtained by performing the first image processing or the second image processing by the image processor on the image data output from the imaging device.

2. The management system as claimed in claim 1, wherein a direction in which the coloring position changes in the plurality of labels is different from the direction separating from the imaging device.

3. The management system as claimed in claim 1, wherein each of the plurality of labels further includes a marker indicating a higher level side and a lower level side of temperature or humidity, and
wherein the image processor is configured to perform the first image processing on the image of the plurality of display parts by using the marker.

4. The management system as claimed in claim 3, wherein the marker is constituted of a pair of markers disposed at respective ends of each of the plurality of display parts, and
wherein the image processor is configured to perform the first image processing so that the number of pixels corresponding to each of the plurality of labels becomes equal to each other among the plurality of labels by transforming the image data in a manner that, when comparing the image of the plurality of display parts before the first image processing is performed with the image of the plurality of display parts after the first image processing is performed, not only each distance between each of the pair of markers becomes equal to each other in the image of the plurality of display parts but also a ratio among distances between two pairs of markers of the labels next to each other becomes equal to a ratio among distances between two pairs of markers of the labels next to each other in actual space.

5. The management system as claimed in claim 4, wherein the plurality of display parts are display parts in which color of one or more display parts corresponding to detected level of temperature or humidity changes into color which is different from color of display parts other than the one or more display parts and
wherein the level detector is configured to extract the one or two display parts where color is changed for each of the plurality of labels in the image data, and detect the level of temperature or humidity based on a ratio between a distance between a position of the extracted one or two display parts and a position corresponding one of the pair of markers and a distance between the position of the extracted one or two display parts and a position corresponding other of the pair of markers for each of the plurality of labels in the image data.

6. The management system as claimed in claim 5, wherein the level detector is configured to detect the level of temperature or humidity by detecting distribution or change of the brightness information based on a degree of change in three primary colors of light emitted from the display parts or a degree of change in light emission obtained by gray-scaling the light emission from the display parts.

7. The management system as claimed in claim 4, wherein, the plurality of display parts are display parts which form an intermediate color which is between a first color and a second color, the first color being formed in one or more display parts indicating a higher side of the level of temperature and humidity, the second color being formed in one or more display parts indicating a lower side of the level of temperature and humidity,
wherein the level detector is configured to locate each position of the plurality of display parts where the intermediate color is formed for each of the plurality of labels in the image data, and detect the level of temperature or humidity based on a ratio between a distance between the position of the display parts where the intermediate color is formed and a position corresponding one of the pair of markers and a distance between the position of the display parts where the intermediate color is formed and a position corresponding other of the pair of markers for each of the plurality of labels in the image data.

8. The management system as claimed in claim 7, wherein the level detector is configured to detect the level of temperature or humidity by detecting distribution or change of the brightness information based on a degree of change in three primary colors of light emitted from the display parts where the intermediate color is formed or a degree of change in light emission obtained by gray-scaling the light emission from the display parts where the intermediate color is formed.

9. The management system as claimed in claim 3, further comprising:
a memory device configured to store the image data of the image of the marker and the plurality of display parts captured by the imaging device;
wherein the level detector is configured to detect the level of temperature or humidity based on a comparison in distribution or change in the brightness information of the image of the plurality of display parts, the image having been identified by performing a pattern matching process on the image of the plurality of display parts and the marker by using the image data stored in the memory device, the image of the plurality of display parts and the marker being an image on which the first image processing or the second image processing has been performed by the image processor.

10. The management system as claimed in claim 1, wherein the level detector is configured to obtain luminance of each of the plurality of labels based on brightness information of the corresponding display parts.

11. The management system as claimed in claim 1, further comprising:
a detector configured to detect a viability status of the living animal by obtaining the image data thereof in time series, in a case where the management target is a living animal.

12. The management system as claimed in claim 1, further comprising:
a detector configured to detect whether there exists an intruder, in a case where the management target is a crop.

13. The management system as claimed in claim 1, wherein the level detector is configured to derive data of temperature or humidity by performing a convolution operation process on the levels of temperature and humidity indicated in a step-by-step manner, so that the derived data of temperature or humidity has finer step width than that of the levels of temperature and humidity.

14. The management system as claimed in claim 1, wherein, the plurality of labels are installed in a direction indicating arrangement of the management target in a manner such that a normal line of the plurality of display parts is in the direction indicating the arrangement of the management target, and
wherein the imaging device unit is disposed in a manner such that a zero degree direction of a view of angle of the imaging device is in a direction indicating an arrangement of the management target.

15. A non-transitory computer-readable recording medium having stored therein a program for causing a computer to execute a management process comprising:
capturing an image of a plurality of labels, each of the plurality of labels including a plurality of display parts configured to change respective colors depending on different levels of temperature or humidity in a step-by-step manner and reversibly, the plurality of display parts being arranged in a predetermined direction and being projected within an image by image processing;
outputting image data indicating the captured image;
performing first image processing or second image processing, the first image processing being configured to transform the image data in a manner such that a number of pixels indicating the image of each of the plurality of labels becomes equal to each other among the plurality of labels in the transformed image data, the second image processing being configured to recognize an image of the plurality of display parts by using size data indicating the plurality of labels; and detecting the levels of temperature or humidity based on brightness information or information indicating a change of brightness of the pixels corresponding to the plurality of display parts in the image data on which the first image processing or the second image processing has been performed.

* * * * *